United States Patent [19]

Kaneko et al.

[11] Patent Number: 5,968,903
[45] Date of Patent: Oct. 19, 1999

[54] **INHIBITION OF *H. PYLORI* PROLIFERATION**

[75] Inventors: Hiroshi Kaneko; Terunori Mitsuma, both of Aichi; Koichi Yamashita, Shizuoka, all of Japan; Barry Morgan, Franklin, Mass.

[73] Assignee: Biomeasure, Incorporated, Milford, Mass.

[21] Appl. No.: 09/074,117

[22] Filed: May 7, 1998

[51] Int. Cl.⁶ .............................. A61K 37/43; C07K 7/26
[52] U.S. Cl. .............................. 514/9; 514/11; 530/311; 530/317; 530/328
[58] Field of Search .................................. 530/311, 328, 530/317; 514/11, 9

[56] References Cited

U.S. PATENT DOCUMENTS

| | | | |
|---|---|---|---|
| 4,133,782 | 1/1979 | Vale, Jr. et al. | 530/311 |
| 4,146,612 | 3/1979 | Veber | 530/311 |
| 4,190,575 | 2/1980 | Sarantakis | 530/311 |
| 4,190,648 | 2/1980 | Veber | 514/11 |
| 4,209,426 | 6/1980 | Sarantakis | 514/11 |
| 4,211,693 | 7/1980 | Rivier et al. | 530/311 |
| 4,215,039 | 7/1980 | Sarantakis | 514/11 |
| 4,224,190 | 9/1980 | Villadsen et al. | 68/163 |
| 4,224,199 | 9/1980 | Meyers et al. | 514/9 |
| 4,235,886 | 11/1980 | Freidinger et al. | 514/11 |
| 4,238,481 | 12/1980 | Rink et al. | 514/11 |
| 4,261,885 | 4/1981 | Sakakibara et al. | 530/311 |
| 4,282,143 | 8/1981 | Sarantakis | 514/11 |
| 4,291,022 | 9/1981 | Sandrin et al. | 530/311 |
| 4,310,518 | 1/1982 | Freidinger et al. | 514/11 |
| 4,316,890 | 2/1982 | Kamber et al. | 514/11 |
| 4,328,214 | 5/1982 | Rink et al. | 514/11 |
| 4,358,439 | 11/1982 | Sieber et al. | 514/11 |
| 4,360,516 | 11/1982 | Freidinger et al. | 514/11 |
| 4,369,179 | 1/1983 | Rink et al. | 514/11 |
| 4,395,403 | 7/1983 | Bauer et al. | 514/11 |
| 4,435,385 | 3/1984 | Bauer et al. | 514/11 |
| 4,485,101 | 11/1984 | Coy et al. | 514/11 |
| 4,486,415 | 12/1984 | Freidinger | 514/11 |
| 4,522,813 | 6/1985 | Nutt | 514/11 |
| 4,585,755 | 4/1986 | Morgan et al. | 514/11 |
| 4,603,120 | 7/1986 | Kamber | 514/11 |
| 4,650,787 | 3/1987 | Schally et al. | 514/11 |
| 4,684,620 | 8/1987 | Hruby et al. | 514/11 |
| 4,725,577 | 2/1988 | Schally et al. | 514/11 |
| 4,728,638 | 3/1988 | Bauer et al. | 514/11 |
| 4,853,371 | 8/1989 | Coy et al. | 514/12 |
| 4,871,717 | 10/1989 | Coy et al. | 514/11 |
| 4,904,642 | 2/1990 | Coy et al. | 514/11 |
| 5,552,520 | 9/1996 | Kim et al. | 530/311 |

FOREIGN PATENT DOCUMENTS

| | | |
|---|---|---|
| 0 030 920 B1 | 6/1981 | European Pat. Off. |
| 0 329 295 A1 | 1/1989 | European Pat. Off. |
| 0 363 589 A2 | 4/1990 | European Pat. Off. |
| 0 389 180 B1 | 9/1990 | European Pat. Off. |
| 0 395 417 B1 | 10/1990 | European Pat. Off. |
| 0 505 680 B1 | 9/1992 | European Pat. Off. |
| 2 522 655 | 3/1982 | France |
| 2 095 261 | 3/1982 | United Kingdom |
| WO 88/027576 | 4/1988 | WIPO |
| WO 90/12811 | 11/1990 | WIPO |
| WO 91/18016 | 4/1991 | WIPO |
| WO 97/01579 | 1/1997 | WIPO |

OTHER PUBLICATIONS

Warren, J.R., et al., The Lancet, Jun. 4, 1983, pp. 1273–1275.
Marshall, B.J., et al., The Lancet, Jun. 16, 1984, pp. 1311–1314.
Rao, R.K., Life Sciences, vol. 48, No. 18, pp. 1685–1704 (1991).
Kaneko, H., et al., Digestive Diseases and Sciences, vol. 37, No. 3. (Mar. 1992), pp. 409–416.
Moss, S.F., et al., The Lancet, vol. 340: Oct. 17, 1992, pp. 930–932.
Calam, J., Annals of Medicine, 27: 569–573, 1995.
Chiba, T., et al., Gut Peptides: Biochemistry and Physiology, eds. John H. Walsh and Graham J. Dockray, Raven Press, Ltd. NY, 1994, pp. 123–145.
Lee, J., et al.,Gastroenterology, 1997; 113: S99–S106.
Gotz, J.M., et al., Scand. J. Gastroenterol., 1995; 30: 1064–1068.
Haruma, K., et al., Scand. J. Gastroenterol., 1995; 30: 550–553.
Alfven, G., et al., Acta Paediatr, 82: 967–970, 1993.
Sumii, M., et al., Am. J. Gastroentero., vol. 89, No. 9, 1994 pp. 1515–1519.
Horvath, A., "Conformation of Somatostatin Analogues Having Antitumor Activity", Peptides, 1992, C.H. Schneider and A.N. Eberle (Eds.) pp.533–534.
Van Binst, Georges and Dirk Tourwe, "Backbone Modifications in Somatostatin Analogues: Relation Between Conformation and Activity", Peptide Research, pp. 8–13.

Primary Examiner—Cecilia J. Tsang
Attorney, Agent, or Firm—John D. Conway; Fish & Richardson

[57] ABSTRACT

The present invention is directed to a method of using somatostatin or a somatostatin agonist to inhibit the proliferation of *Helicobacter pylori* (*H. pylori*), which comprises administering to a patient in need thereof an effective amount of said somatostatin or somatostatin agonist. Preferably, a somatostatin sub-type receptor 2 (SSTR-2) selective somatostatin agonist is administered in a method of this invention. The inhibition of *H. pylori* proliferation is useful in treating various gastroduodenal diseases such as peptic ulcers, gastric cancer and gastric lymphoma.

41 Claims, No Drawings

INHIBITION OF *H. PYLORI* PROLIFERATION

BACKGROUND OF THE INVENTION

The present invention is directed to a method of using somatostatin or a somatostatin analogue to inhibit the proliferation of *Helicobacter pylori* (*H. pylori*), which comprises administering to a patient in need thereof an effective amount of said somatostatin or somatostatin analogue. Preferably, a somatostatin sub-type receptor 2 (SSTR-2) selective somatostatin analogue is administered in a method of this invention.

A growing body of evidence supports a crucial etiological role of *H. pylori* in the pathogenesis of various gastroduodenal diseases and disorders such as peptic ulcers, gastric cancer, gastric lymphoma, MALT (mucosa-associated lymphoid tissue) lymphoma, gastritis with severe abnormality and after early gastric cancer resection. *H. pylori* can only survive in the gastric mucous layer covering the gastric epithelial cells (Warren, J. R., Marshall, B. J., Lancet, 1983;1:1273–1275, and Marshall, B. J., Warren, J. R., Lancet, 1984;1:1311–1314). Several bioactive peptides such as gastrin and somatostatin, which exist not only in the gastric mucosa (gastrin-containing G-cells and somatostatin containing D-cells) but also in gastric juice, play an important pathophysiological role in gastroduodenal function (Rao, R. K., Life Sci., 1991;48:1685–1704). It has been demonstrated that levels of somatostatin-like immunoreactivity both in the antral mucosa and in gastric juice are lower in subjects infected with *H. pylori* compared with *H. pylori* negative subjects (Kaneko, H., et al., Dig. Dis. Sci. 1992;37:409–416). Others have demonstrated that *H. pylori* infection decreases mucosal somatostatin content, D-cell number and somatostatin messenger RNA (mRNA) expression and that eradication of *H. pylori* reverses the somatostatin-related parameters mentioned above (Moss, S. F., et al., Lancet, 1992; 340:930–932; Sumii, M., et al., Am. J. Gastroenterol., 1994;89:1515–1519; Calam. J., Ann. Med. 1995;27:569–573). From these lines of evidence, somatostatin-linked pathogenesis in *H. pylori*-induced mucosal damage has been proposed. Moreover, somatostatin not only shows gastroprotective property by decreasing acid secretion mediated via inhibiting gastrin secretion, but also regulates the proliferation and differentiation of several lines of cells (Chiba, T., Yamada, T., Gut somatostatin. In: Walsh, J. H., Dockray, G. J., ed., Gut peptides: Biochemistry and Physiology. New York: Raven, 1994:123–145). However, an effect of somatostatin on *H. pylori* proliferation remains unknown.

As a cure for *H. pylori* infection in several gastroduodenal diseases, treatment with certain drugs have been used, such as amoxycillin, clarithromycin, metronidazole and tinidazole, but the current pharmaceutical treatments have undesirable side-effects (Lee, J., O'Morain, C., Gastroenterology, 1997;113:S99–S106). Thus, there is a need for a drug which avoids the undesirable side-effects.

SUMMARY OF THE INVENTION

In one aspect, the present invention is directed to a method of inhibiting the proliferation of *H. pylori* in a patient in need thereof, which comprises administering to said patient an effective amount of somatostatin or a somatostatin agonist or a pharmaceutically acceptable salt thereof. In another aspect, this invention provides a method of treating a medical disorder associated with the proliferation of *H. pylori* in a patient in need thereof, which comprises administering an effective amount of somatostatin or a somatostatin agonist or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

A preferred method of inhibiting the proliferation of *H. pylori* in a patient in need thereof, is where somatostatin is administered to said patient. In another aspect, this invention provides a method of treating a medical disorder associated with the proliferation of *H. pylori* in a patient in need thereof, which comprises administering an effective amount of somatostatin or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Another preferred method of inhibiting the proliferation of *H. pylori* in a patient in need thereof, is where a somatostatin agonist or a pharmaceutically acceptable salt thereof is administered to said patient. In another aspect, this invention provides a method of treating a medical disorder associated with the proliferation of *H. pylori* in a patient in need thereof, which comprises administering an effective amount of a somatostatin agonist or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

A more preferred method of inhibiting the proliferation of *H. pylori* in a patient in need thereof, is where the somatostatin agonist is a somatostatin sub-type receptor 2 selective agonist or a pharmaceutically acceptable salt thereof which is administered to said patient. In another aspect, this invention provides a method of treating a medical disorder associated with the proliferation of *H. pylori* in a patient in need thereof, which comprises administering an effective amount of a somatostatin sub-type receptor 2 selective agonist or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

An even more preferred method of inhibiting the proliferation of *H. pylori* in a patient in need thereof, is where the somatostatin sub-type receptor 2 selective agonist cyclo(N-Me-Ala-Tyr-D-Trp-Lys-Val-Phe) or H-D-β-Nal-Cys-Tyr-D-Trp-Lys-Thr-Cys-Thr-NH$_2$ or a pharmaceutically acceptable salt thereof is administered to said patient. In another aspect, this invention provides a method of treating a medical disorder associated with the proliferation of *H. pylori* in a patient in need thereof, which comprises administering an effective amount of cyclo(N-Me-Ala-Tyr-D-Trp-Lys-Val-Phe) or H-D-β-Nal-Cys-Tyr-D-Trp-Lys-Thr-Cys-Thr-NH$_2$ or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Another even more preferred method of inhibiting the proliferation of *H. pylori* in a patient in need thereof, is where the somatostatin agonist H-Cys-Phe-Phe-D-Trp-Lys-Thr-Phe-Cys-NH$_2$ or H-Cys-Phe-Tyr-D-Trp-Lys-Thr-Phe-Cys-NH$_2$ or a pharmaceutically acceptable salt thereof is administered to said patient. In another aspect, this invention provides a method of treating a medical disorder associated with the proliferation of H. pylori in a patient in need thereof, which comprises administering an effective amount of H-Cys-Phe-Phe-D-Trp-Lys-Thr-Phe-Cys-NH$_2$ or H-Cys-Phe-Tyr-D-Trp-Lys-Thr-Phe-Cys-NH$_2$ or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Another preferred method of inhibiting the proliferation of H. pylori in a patient in need thereof, is where the somatostatin agonist is a compound selected from the compounds listed as Examples 2–75, 77–106, 108, 110 and 122–149, shown hereinbelow, or a pharmaceutically acceptable salt thereof is administered to said patient. In another aspect, this invention provides a method of treating a medical disorder associated with the proliferation of H. pylori in a patient in need thereof, which comprises administering an effective amount of a compound selected from the compounds listed as Examples 2–75, 77–106, 108, 110 and 122–149 or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Yet another preferred method of inhibiting the proliferation of H. pylori in a patient in need thereof, is where the somatostatin agonist that is administered is a compound of the formula (I) or a pharmaceutically acceptable salt thereof as defined hereinbelow. A preferred group of compounds of a compound of formula (I) are H-D-Phe-p-chloro-Phe-Tyr-D-Trp-Lys-Thr-Phe-Thr-NH$_2$, H-D-Phe-p-NO$_2$-Phe-Tyr-D-Trp-Lys-Val-Phe-Thr-NH$_2$, H-D-β-Nal-p-chloro-Phe-Tyr-D-Trp-Lys-Val-Phe-Thr-NH$_2$, H-D-Phe-Phe-Tyr-D-Trp-Lys-Val-Phe-Thr-NH$_2$, H-D-Phe-p-chloro-Phe-Tyr-D-Trp-Lys-Val-Phe-Thr-NH$_2$, and H-D-Phe-Ala-Tyr-D-Trp-Lys-Val-Ala-D-P-Nal-NH$_2$ or a pharmaceutically acceptable salt thereof. In another aspect, this invention provides a method of treating a medical disorder associated with the proliferation of H. pylori in a patient in need thereof, which comprises administering an effective amount of a compound of formula (I) or a preferred compound of formula (I) (see above) or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Still another preferred method of inhibiting the proliferation of H. pylori in a patient in need thereof is where the somatostatin agonist that is administered is

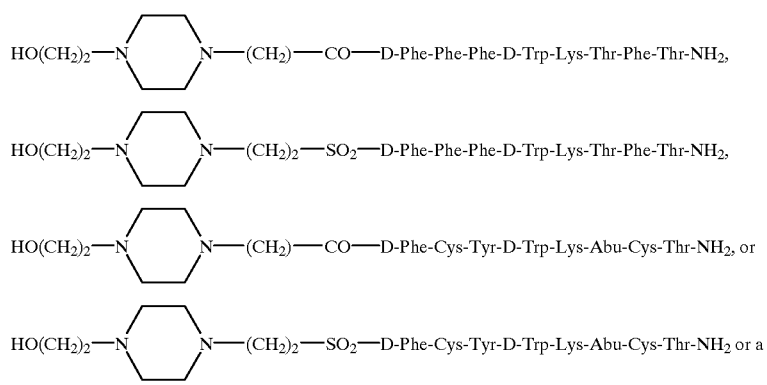

pharmaceutically acceptable salt thereof. In another aspect, this invention provides a method of treating a medical disorder associated with the proliferation of H. pylori in a patient in need thereof, which comprises administering an effective amount of a compound shown immediately above or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Even still another preferred method of inhibiting the proliferation of H. pylori in a patient in need thereof is where the somatostatin agonist that is administered is a compound of the formula (II), as defined hereinbelow, or a pharmaceutically acceptable salt thereof. In another aspect, this invention provides a method of treating a medical disorder associated with the proliferation of H. pylori in a patient in need thereof, which comprises administering an effective amount of a compound of the formula (II) or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

Even still another preferred method of inhibiting the proliferation of H. pylori in a patient in need thereof, is where the somatostatin agonist that is administered is a compound of the formula (III), as defined hereinbelow, or a pharmaceutically acceptable salt thereof. In another aspect, this invention provides a method of treating a medical disorder associated with the proliferation of *H. pylori* in a patient in need thereof, which comprises administering an effective amount of a compound of the formula (Ill) or a pharmaceutically acceptable salt thereof to said patient. A preferred method of the immediately foregoing method is where the medical disorder is peptic ulcer disease, mucosa-associated lymphoid tissue lymphoma, gastritis with severe abnormality, treatment after early gastric cancer resection, gastric cancer and gastric lymphoma.

In another aspect, this invention provides a pharmaceutical composition comprising an effective amount of somatostatin or a somatostatin agonist or a pharmaceutically acceptable salt thereof sufficient for inhibiting the proliferation of *H. pylori*, and a pharmaceutically acceptable carrier. A preferred pharmaceutical composition is where the somatostatin agonist is a somatostatin sub-type receptor 2 selective agonist or a pharmaceutically acceptable salt thereof. A preferred pharmaceutical composition of the immediately foregoing composition is where the somatostatin sub-type receptor 2 selective agonist is cyclo(N-Me-Ala-Tyr-D-Trp-Lys-Val-Phe), H-D-β-Nal-Cys-Tyr-D-Trp-Lys-Thr-Cys-Thr-NH$_2$, 10 nM, or less than 2 nM, or of less than 1 nM) for the SSTR-5 or SSTR-2, respectively (e.g., as defined by the receptor binding assay described below). The somatostatin agonist may also be selective for a particular somatostatin receptor, e.g., have a higher binding affinity for a particular somatostatin receptor subtype as compared to the other receptor subtypes. What is meant by, for example, an SSTR-5 selective agonist is a somatostatin agonist which has a higher binding affinity (i.e., Ki) for SSTR-5 than for either SSTR-1, SSTR-2, SSTR-3, or SSTR-4.

Somatostatin agonists which can be used to practice a method of the present invention include, but are not limited to, those covered by formulae or those specifically recited in the publications set forth below, the teachings of which are hereby incorporated by reference:

Van Binst, G. et al. Peptide Research 5:8 (1992);
Horvath, A. et al. Abstract, "Conformations of Somatostatin Analogs Having Antitumor Activity", 22nd European peptide Symposium, Sep. 13–19, 1992, Interlaken, Switzerland;
U.S. Pat. No. 5,506,339 (1996);
EP Application 0 363 589 A2 (1990);

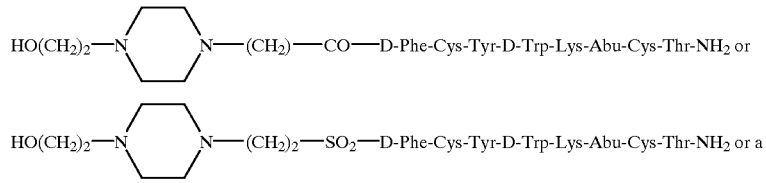

pharmaceutically acceptable salt thereof.

Another preferred pharmaceutical composition is where the somatostatin agonist is H-Cys-Phe-Phe-D-Trp-Lys-Thr-Phe-Cys-NH$_2$ or H-Cys-Phe-Tyr-D-Trp-Lys-Thr-Phe-Cys-NH$_2$, or a pharmaceutically acceptable salt thereof.

Yet another preferred pharmaceutical composition comprises an effective amount of somatostatin or a pharmaceutically acceptable salt thereof sufficient to inhibit the proliferation of *H. pylori*, and a pharmaceutically acceptable carrier.

DETAILED DESCRIPTION

Somatostatin (somatotropin release inhibiting factor or SRIF) has both a 14 amino acid isoform (somatostatin-14) and a 28 amino acid isoform (somatostatin-28) (Wilson, J. & Foster, D., *Williams Textbook of Endocrinology*, p. 510 7th ed., 1985). The compound is an inhibitor of secretion of growth hormone and was originally isolated from the hypothalamus (Brazeau, et al., Science 179:77, 1973). Native somatostatin has a very short duration of effect in vivo since it is rapidly inactivated by endo- and exopeptidase. Many novel analogs have been prepared in order to enhance the duration of effect, biological activity, and selectivity (e.g., for the particular somatostatin receptor) of this hormone. Such analogs will be called "somatostatin agonists" herein.

Various somatostatin receptors (SSTRs) have been isolated, e.g., SSTR-1, SSTR-2, SSTR-3, SSTR-4, and SSTR-5. Thus, the somatostatin agonist may be a SSTR-1 agonist, SSTR-2 agonist, SSTR-3 agonist, SSTR-4 agonist or an SSTR-5 agonist. In one embodiment, the somatostatin agonist of the present invention is an SSTR-5 agonist or an SSTR-2 agonist. What is meant by an "SSTR-5 agonist" or an "SSTR-2 agonist" is a compound which has a high affinity (e.g., Ki of less than 1 μM or, preferably, of less than U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
U.S. Pat. No. 4,725,577 (1988);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,190 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);

U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
U.S. Pat. No. 5,552,520 (1996);
EP Patent No. 0 389 180 (1990);
EP Application No. 0 505 680 (1982);
U.S. Pat. No. 4,603,120 (1986);
EP Application No. 0 030 920 (1980);
U.S. Pat. No. 4,871,717 (1989);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Note that for all somatostatin agonists described herein, each amino acid residue represents the structure of —NH—C(R)H—CO—, in which R is the side chain (e.g., $CH_3$ for Ala) except for Thr-ol which means —NH—CH(CH($CH_3$)OH)—$CH_2$—OH and Pro which means prolinyl. Lines between amino acid residues represent peptide bonds which join the amino acids. Also, where the amino acid residue is optically active, it is the L-form configuration that is intended unless the D-form is expressly designated. A disulfide bridge is formed between the two free thiols (e.g., Cys, Pen, or Bmp residues) when they are present in a peptide; however, the disulfide bond is not shown.

The methods for synthesizing peptides such as somatostatin agonists are well documented and are within the ability of a person of ordinary skill in the art, as illustrated by the patents cited hereinabove. For example, synthesis of H-D-Phe-Phe-Phe-D-Trp-Lys-Thr-Phe-Thr-$NH_2$, described above, can be achieved by following the protocol set forth in Example I of European Patent Application 0 395 417 A1. The synthesis of somatostatin agonists with a substituted N-terminus can be achieved, for example, by following the protocol set forth in WO 88/02756, European Patent Application No. 0 329 295, and U.S. Pat. No. 5,240,561.

Examples of somatostatin agonists that can be used in a method of this invention include, but are not limited to, the following somatostatin analogs which are disclosed in the above-cited references:

Example 1: H-D-β-Nal-Cys-Tyr-D-Trp-Lys-Thr-Cys-Thr-$NH_2$;
Example 2: H-D-Phe-Cys-Phe-D-Trp-Lys-Thr-Cys-β-Nal-$NH_2$;
Example 3: H-D-Phe-Cys-Tyr-D-Trp-Lys-Thr-Cys-β-Nal-$NH_2$;
Example 4: H-D-β-Nal-Cys-Phe-D-Trp-Lys-Thr-Cys-Thr-$NH_2$;
Example 5: H-D-Phe-Cys-Tyr-D-Trp-Lys-Thr-Pen-Thr-$NH_2$;
Example 6: H-D-Phe-Cys-Phe-D-Trp-Lys-Thr-Pen-Thr-$NH_2$;
Example 7: H-D-Phe-Cys-Tyr-D-Trp-Lys-Thr-Pen-Thr-OH;
Example 8: H-D-Phe-Cys-Phe-D-Trp-Lys-Thr-Pen-Thr-OH;
Example 9: H-Gly-Pen-Phe-D-Trp-Lys-Thr-Cys-Thr-OH;
Example 10: H-Phe-Pen-Tyr-D-Trp-Lys-Thr-Cys-Thr-OH;
Example 11: H-Phe-Pen-Phe-D-Trp-Lys-Thr-Pen-Thr-OH;
Example 12: H-D-Phe-Cys-Phe-D-Trp-Lys-Thr-Cys-Thr-ol;
Example 13: H-D-Phe-Cys-Phe-D-Trp-Lys-Thr-Cys-Thr-$NH_2$;
Example 14: H-D-Trp-Cys-Tyr-D-Trp-Lys-Val-Cys-Thr-$NH_2$;
Example 15: H-D-Trp-Cys-Phe-D-Trp-Lys-Thr-Cys-Thr-$NH_2$;
Example 16: H-D-Phe-Cys-Tyr-D-Trp-Lys-Val-Cys-Thr-$NH_2$;
Example 17: H-D-Phe-Cys-Tyr-D-Trp-Lys-Val-Cys-Trp-$NH_2$;
Example 18: H-D-Phe-Cys-Tyr-D-Trp-Lys-Val-Cys-Thr-$NH_2$;
Example 19: Ac-D-Phe-Lys*-Tyr-D-Trp-Lys-Val-Asp*-Thr-$NH_2$ (an amide bridge formed between Lys* and Asp*);
Example 20: Ac-hArg(Et)$_2$-Gly-Cys-Phe-D-Trp-Lys-Thr-Cys-Thr-$NH_2$;
Example 21: Ac-D-hArg(Et)$_2$-Gly-Cys-Phe-D-Trp-Lys-Thr-Cys-Thr-$NH_2$;
Example 22: Ac-D-hArg(Bu)-Gly-Cys-Phe-D-Trp-Lys-Thr-Cys-Thr-$NH_2$;
Example 23: Ac-D-hArg(Et)$_2$-Cys-Phe-D-Trp-Lys-Thr-Cys-Thr-$NH_2$;
Example 24: Ac-L-hArg(Et)$_2$-Cys-Phe-D-Trp-Lys-Thr-Cys-Thr-$NH_2$;
Example 25: Ac-D-hArg($CH_2CF_3$)$_2$-Cys-Phe-D-Trp-Lys-Thr-Cys-Thr-$NH_2$;
Example 26: Ac-D-hArg($CH_2CF_3$)$_2$-Gly-Cys-Phe-D-Trp-Lys-Thr-Cys-Thr-$NH_2$;
Example 27: Ac-D-hArg($CH_2CF_3$)$_2$-Gly-Cys-Phe-D-Trp-Lys-Thr-Cys-Phe-$NH_2$;
Example 28: Ac-D-hArg($CH_2CF_3$)$_2$-Gly-Cys-Phe-D-Trp-Lys-Thr-Cys-Thr-NHEt;
Example 29: Ac-L-hArg($CH_2$-$CF_3$)$_2$-Gly-Cys-Phe-D-Trp-Lys-Thr-Cys-Thr-$NH_2$;
Example 30: Ac-D-hArg($CH_2CF_3$)$_2$-Gly-Cys-Phe-D-Trp-Lys(Me)-Thr-Cys-Thr-$NH_2$;
Example 31: Ac-D-hArg($CH_2CF_3$)$_2$-Gly-Cys-Phe-D-Trp-Lys(Me)-Thr-Cys-Thr-N H Et;
Example 32: Ac-hArg($CH_3$, hexyl)-Gly-Cys-Phe-D-Trp-Lys-Thr-Cys-Thr-$NH_2$;
Example 33: H-hArg(hexyl$_2$)-Gly-Cys-Phe-D-Trp-Lys-Thr-Cys-Thr-$NH_2$;
Example 34: Ac-D-hArg(Et)$_2$-Gly-Cys-Phe-D-Trp-Lys-Thr-Cys-Thr-NHEt;
Example 35: Ac-D-hArg(Et)$_2$-Gly-Cys-Phe-D-Trp-Lys-Thr-Cys-Phe-$NH_2$;
Example 36: Propionyl-D-hArg(Et)$_2$-Gly-Cys-Phe-D-Trp-Lys(iPr)-Thr-Cys-Thr-$NH_2$;
Example 37: Ac-D-p-Nal-Gly-Cys-Phe-D-Trp-Lys-Thr-Cys-Gly-hArg(Et)$_2$-N $H_2$;
Example 38: Ac-D-Lys(iPr)-Gly-Cys-Phe-D-Trp-Lys-Thr-Cys-Thr-$NH_2$;
Example 39: Ac-D-hArg($CH_2CF_3$)$_2$-D-hArg($CH_2CF_3$)$_2$-Gly-Cys-Phe-D-Trp-Lys-Thr-Cys-Thr-$NH_2$;
Example 40: Ac-D-hArg($CH_2CF_3$)$_2$-D-hArg($CH_2CF_3$)$_2$-Gly-Cys-Phe-D-Trp-Lys-Thr-Cys-Phe-$NH_2$;
Example 41: Ac-D-hArg(Et)$_2$-D-hArg(Et)$_2$-Gly-Cys-Phe-D-Trp-Lys-Thr-Cys-Thr-$NH_2$;

Example 42: Ac-Cys-Lys-Asn-4-Cl-Phe-Phe-D-Trp-Lys-Thr-Phe-Thr-Ser-D-Cys-NH$_2$;
Example 43: H-Bmp-Tyr-D-Trp-Lys-Val-Cys-Thr-NH$_2$;
Example 44: H-Bmp-Tyr-D-Trp-Lys-Val-Cys-Phe-NH$_2$;
Example 45: H-Bmp-Tyr-D-Trp-Lys-Val-Cys-p-Cl-Phe-NH$_2$;
Example 46: H-Bmp-Tyr-D-Trp-Lys-Val-Cys-p-Nal-NH$_2$;
Example 47: H-D-p-Nal-Cys-Tyr-D-Trp-Lys-Val -Cys-ThrN H$_2$;
Example 48: H-D-Phe-Cys-Tyr-D-Trp-Lys-Abu-Cys-Thr-NH$_2$;
Example 49: H-D-Phe-Cys-Tyr-D-Trp-Lys-Abu-Cys-β-Nal-NH$_2$;
Example 50: H-pentafluoro-D-Phe-Cys-Tyr-D-Trp-Lys-Val-Cys-Thr-N H$_2$;
Example 51: Ac-D-β-Nal-Cys-pentafluoro-Phe-D-Trp-Lys-Val-Cys-Thr-NH$_2$;
Example 52: H-D-β-Nal-Cys-Tyr-D-Trp-Lys-Val-Cys-β-Nal-NH$_2$;
Example 53: H-D-Phe-Cys-Tyr-D-Trp-Lys-Val-Cys-p-Nal-NH$_2$;
Example 54: H-D-β-Nal-Cys-Tyr-D-Trp-Lys-Abu-Cys-Thr-NH$_2$;
Example 55: H-D-p-Cl-Phe-Cys-Tyr-D-Trp-Lys-Abu-Cys-Thr-NH$_2$;
Example 56: Ac-D-p-CL-Phe-Cys-Tyr-D-Trp-Lys-Abu-Cys-Thr-N H$_2$;
Example 57: H-D-Phe-Cys-β-Nal-D-Trp-Lys-Val-Cys-Thr-NH$_2$;
Example 58: H-D-Phe-Cys-Tyr-D-Trp-Lys-Cys-Thr-NH$_2$;
Example 59: cyclo(Pro-Phe-D-Trp-N-Me-Lys-Thr-Phe);
Example 60: cyclo(Pro-Phe-D-Trp-N-Me-Lys-Thr-Phe);
Example 61: cyclo(Pro-Phe-D-Trp-Lys-Thr-N-Me-Phe);
Example 62: cyclo(N-Me-Ala-Tyr-D-Trp-Lys-Thr-Phe);
Example 63: cyclo(Pro-Tyr-D-Trp-Lys-Thr-Phe);
Example 64: cyclo(Pro-Phe-D-Trp-Lys-Thr-Phe);
Example 65: cyclo(Pro-Phe-L-Trp-Lys-Thr-Phe);
Example 66: cyclo(Pro-Phe-D-Trp(F)-Lys-Thr-Phe);
Example 67: cyclo(Pro-Phe-Trp(F)-Lys-Thr-Phe);
Example 68: cyclo(Pro-Phe-D-Trp-Lys-Ser-Phe);
Example 69: cyclo(Pro-Phe-D-Trp-Lys-Thr-p-Cl-Phe);
Example 70: cyclo(D-Ala-N-Me-D-Phe-D-Thr-D-Lys-Trp-D-Phe);
Example 71: cyclo(D-Ala-N-Me-D-Phe-D-Val-Lys-D-Trp-D-Phe);
Example 72: cyclo(D-Ala-N-Me-D-Phe-D-Thr-Lys-D-Trp-D-Phe);
Example 73: cyclo(D-Abu-N-Me-D-Phe-D-Val-Lys-D-Trp-D-Tyr);
Example 74: cyclo(Pro-Tyr-D-Trp-t-4-AchxAla-Thr-Phe);
Example 75: cyclo(Pro-Phe-D-Trp-t-4-AchxAla-Thr-Phe);
Example 76: cyclo(N-Me-Ala-Tyr-D-Trp-Lys-Val-Phe);
Example 77: cyclo(N-Me-Ala-Tyr-D-Trp-t-4AchxAla-Thr-Phe);
Example 78: cyclo(Pro-Tyr-D-Trp-4-Amphe-Thr-Phe);
Example 79: cyclo(Pro-Phe-D-Trp-4-Amphe-Thr-Phe);
Example 80: cyclo(N-Me-Ala-Tyr-D-Trp-4-Amphe-Thr-Phe);
Example 81: cyclo(Asn-Phe-Phe-D-Trp-Lys-Thr-Phe-Gaba);
Example 82: cyclo(Asn-Phe-Phe-D-Trp-Lys-Thr-Phe-Gaba-Gaba);
Example 83: cyclo(Asn-Phe-D-Trp-Lys-Thr-Phe);
Example 84: cyclo(Asn-Phe-Phe-D-Trp-Lys-Thr-Phe-NH (CH$_2$)$_4$CO);
Example 85: cyclo(Asn-Phe-Phe-D-Trp-Lys-Thr-Phe-β-Ala);
Example 86: cyclo(Asn-Phe-Phe-D-Trp-Lys-Thr-Phe-D-Glu)-OH;
Example 87: cyclo(Phe-Phe-D-Trp-Lys-Thr-Phe);
Example 88: cyclo(Phe-Phe-D-Trp-Lys-Thr-Phe-Gly);
Example 89: cyclo(Phe-Phe-D-Trp-Lys-Thr-Phe-Gaba);
Example 90: cyclo(Asn-Phe-Phe-D-Trp-Lys-Thr-Phe-Gly);
Example 91: cyclo(Asn-Phe-Phe-D-Trp(F)-Lys-Thr-Phe-Gaba);
Example 92: cyclo(Asn-Phe-Phe-D-Trp(NO$_2$)-Lys-Thr-Phe-Gaba);
Example 93: cyclo(Asn-Phe-Phe-Trp(Br)-Lys-Thr-Phe-Gaba);
Example 94: cyclo(Asn-Phe-Phe-D-Trp-Lys-Thr-Phe(l)-Gaba);
Example 95: cyclo(Asn-Phe-Phe-D-Trp-Lys-Thr-Tyr(But)-Gaba);
Example 96: cyclo(Bmp-Lys-Asn-Phe-Phe-D-Trp-Lys-Thr-Phe-Thr-Pro-Cys)-OH;
Example 97: cyclo(Bmp-Lys-Asn-Phe-Phe-D-Trp-Lys-Thr-Phe-Thr-Pro-Cys)-OH;
Example 98: cyclo(Bmp-Lys-Asn-Phe-Phe-D-Trp-Lys-Thr-Phe-Thr-Tpo-Cys)-OH;
Example 99: cyclo(Bmp-Lys-Asn-Phe-Phe-D-Trp-Lys-Thr-Phe-Thr-MeLeu-Cys)-OH;
Example 100: cyclo(Phe-Phe-D-Trp-Lys-Thr-Phe-Phe-Gaba);
Example 101: cyclo(Phe-Phe-D-Trp-Lys-Thr-Phe-D-Phe-Gaba);
Example 102: cyclo(Phe-Phe-D-Trp(5F)-Lys-Thr-Phe-Phe-Gaba);
Example 103: cyclo(Asn-Phe-Phe-D-Trp-Lys(Ac)-Thr-Phe-NH—(CH$_2$)$_3$-CO);
Example 104: cyclo(Lys-Phe-Phe-D-Trp-Lys-Thr-Phe-Gaba);
Example 105: cyclo(Lys-Phe-Phe-D-Trp-Lys-Thr-Phe-Gaba);
Example 106: cyclo(Orn-Phe-Phe-D-Trp-Lys-Thr-Phe-Gaba);
Example 107: H-Cys-Phe-Phe-D-Trp-Lys-Thr-Phe-Cys-NH$_2$;
Example 108: H-Cys-Phe-Phe-D-Trp-Lys-Ser-Phe-Cys-NH$_2$;
Example 109: H-Cys-Phe-Tyr-D-Trp-Lys-Thr-Phe-Cys-NH$_2$; and
Example 110: H-Cys-Phe-Tyr(l)-D-Trp-Lys-Thr-Phe-Cys-NH$_2$.

Use of a linear somatostatin agonist of the formula (I) in a method of this invention is also within the scope of this invention:

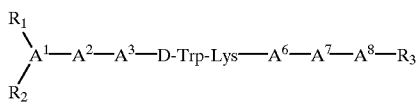 (I)

wherein $A^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^3$ is pyridyl-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$ or $NO_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$;

each $R_1$ and $R_2$, independently, is H, lower acyl or lower alkyl; and $R_3$ is OH or $NH_2$.

Specific examples of linear agonists that can be used in a method of this invention include:

Example 111: H-D-Phe-p-chloro-Phe-Tyr-D-Trp-Lys-Thr-Phe-Thr-N $H_2$;

Example 112: H-D-Phe-p-$NO_2$-Phe-Tyr-D-Trp-Lys-Val-Phe-Thr-$NH_2$;

Example 113: H-D-P-Nal-p-chloro-Phe-Tyr-D-Trp-Lys-Val-Phe-Thr-$NH_2$;

Example 114: H-D-Phe-Phe-Phe-D-Trp-Lys-Thr-Phe-Thr-$NH_2$;

Example 115: H-D-Phe-Phe-Tyr-D-Trp-Lys-Val-Phe-Thr-$NH_2$;

Example 116: H-D-Phe-p-chloro-Phe-Tyr-D-Trp-Lys-Val-Phe-Thr-$NH_2$; and

Example 117: H-D-Phe-Ala-Tyr-D-Trp-Lys-Val-Ala-D-β-Nal-$NH_2$.

If desired, one or more chemical moieties, e.g., a sugar derivative, mono or poly-hydroxy ($C_{2-12}$) alkyl, mono or poly-hydroxy ($C_{2-12}$) acyl groups, or a piperazine derivative, can be attached to a somatostatin agonist, e.g., to the N-terminus amino acid. See PCT Application WO 88/02756, European Application 0 329 295, and U.S. Pat. No. 5,240,561. Examples of somatostatin agonists which contain N-terminal chemical substitutions that can be used in a method of this invention are:

Example 118:

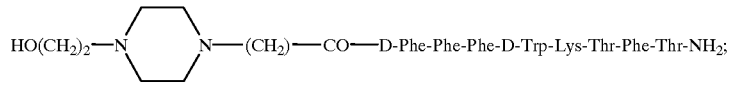

Example 119:

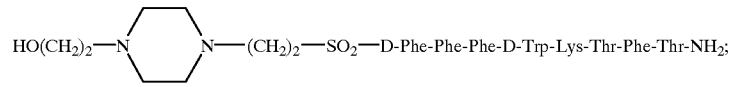

Example 120

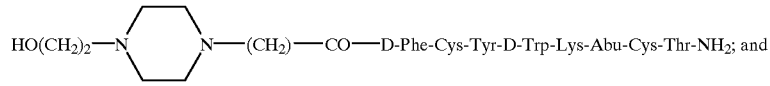

Example 121

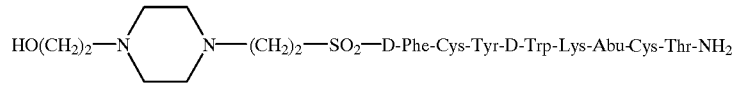

Another set of compounds that can be used in a method the present invention is a compound of the formula (II)

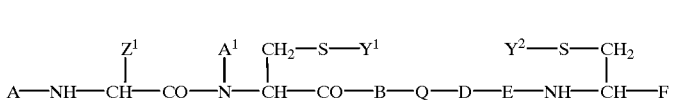

(II)

or a pharmaceutically acceptable salt thereof,
wherein
A is hydrogen, $(C_1-C_3)$alkyl, $(C_1-C_4)$alkanoyl;
$Z^1$ is —$(CH_2)_n$Ar wherein Ar is an aromatic side chain moiety of an aromatic amino acid or a lipophilic side chain moiety of a lipophilic amino acid, wherein the aromatic side chain is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy; n is 1, 2 or 3;
$A^1$ is hydrogen or $(C_1-C_3)$alkyl;
$Y^1$ and $Y^2$ are each independently hydrogen;
or $Y^1$ and $Y^2$ are taken together to form a bond between the sulfur atoms to which they are attached;
B is an aromatic amino acid wherein the aromatic side chain moiety is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy;
Q is L- or D-Trp which is optionally substituted in the benzene ring by F, Cl, Br, $NO_2$, $NH_2$, OH, $(C_1-C_3)$alkyl or $(C_1-C_3)$alkoxy;
D is Lys or Orn wherein the α-amino group is optionally substituted by methyl and the δ-$NH_2$ is optionally substituted by $(C_1-C_3)$alkyl;
E is Ser, Thr or an amino acid having a side chain portion which is $(C_1-C_5)$alkyl, $(C_5-C_7)$cycloalkyl-$(C_1-C_2)$alkyl or —$(CH_2)_m$-Aryl wherein m is 1, 2 or 3 and the Aryl group is phenyl, naphthyl, indolyl or a heterocyclyl group which is a 5 or 6 membered aromatic ring where one or more carbons are replaced with N, O or S, where the Aryl group is optionally substituted by one to five substituents each independently selected from the group consisting of halogen, $NO_2$, $NH_2$, OH, $(C_1-C_3)$alkyl and $(C_1-C_3)$alkoxy;

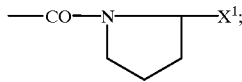

F is $COOR^1$, $CH_2OR^2$, CO—$NR^3R^4$ or
wherein $R^1$ is hydrogen or $(C_1-C_3)$alkyl; $R^2$ is hydrogen or the radical of a physiologically acceptable, physiologically hydrolyzable ester; $R^3$ is hydrogen, $(C_1-C_3)$alkyl, phenyl or phenyl-$(C_1-C_3)$alkyl, provided that when $R^4$ is —CH($R^5$)—$X^1$ then $R^3$ can only be hydrogen or $(C_1-C_3)$ alkyl; $R^4$ is hydrogen, $(C_1-C_3)$alkyl or —CH($R^5$)—$X^1$; $R^5$ is the side chain of a natural amino acid, HO—$(CH_2)_2$— or HO—$(CH_2)_3$—; $X^1$ is $COOR^1$, $CH_2OR^2$ or CO—$NR^6R^7$; $R^6$ is hydrogen or $(C_1-C_3)$alkyl; $R^7$ is hydrogen, $(C_1-C_3)$ alkyl, phenyl or phenyl-$(C_1-C_3)$alkyl.
Yet another compound that can be used in a method the present invention is a compound of the formula (III),

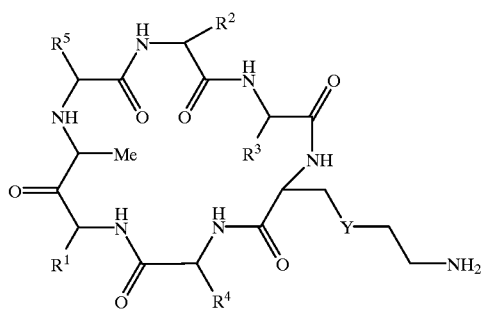

(III)

or a pharmaceutically acceptable salt thereof,
wherein
Y is $(CH_2)_m$ wherein m is 0, 1 or 2 or sulfur such that the sulfur may be in any position along the chain;
$R^1$ and $R^2$ are independently $(C_1-C_5)$alkyl, benzyl, substituted benzyl where the substituent may be one or two of $(C_1-C_5)$alkyl, halogen, hydroxy, amino, nitro or $(C_1-C_5)$ alkoxy; and $(C_1-C_5)$alkyl substituted with a 5- or 6-membered heterocyclic ring having 1 or 2 heteroatoms selected from the group consisting of O, N and S;
$R^3$ is 3-indolylmethyl or substituted 3-indolylmethyl wherein the substituent may be $(C_1-C_5)$alkyl, $(C_1-C_5)$ alkoxy or halogen;
$R^4$ is $(C_1-C_5)$alkyl, hydroxy-$(C_1-C_5)$alkyl, benzyl, carboxy-$(C_1-C_5)$alkyl, amino-$(C_1-C_5)$alkyl or substituted benzyl wherein the substituent may be $(C_1-C_5)$alkyl, $(C_1-C_5)$alkoxy, hydroxy, halogen, amino or nitro; and
$R^5$ is hydrogen, $(C_1-C_5)$alkyl, benzyl, or substituted benzyl wherein the substituent is $(C_1-C_5)$alkyl, $(C_1-C_5)$alkoxy, hydroxy, halogen, amino or nitro.
Further examples of somatostatin agonists that can be used in a method of this invention include the following somatostatin analogues which are disclosed in the references cited herein and can be made according to standard peptide synthesis methods known to those of ordinary skill in the art:
Example 122: D-Cpa-cyclo[Cys-Tyr-D-Trp-Lys-Val-Cys]-Thr-$NH_2$;
Example 123: D-Phe-cyclo[Cys-Tyr-D-Trp-Lys-Val-Cys]-Thr-$NH_2$;
Example 124: D-Phe-cyclo[Cys-p-$NH_2$-Phe-D-Trp-Lys-Val-Cys]-Thr-$NH_2$;
Example 125: N-Me-D-Phe-cyclo[Cys-Tyr-D-Trp-Lys-Val-Cys]-Thr-$NH_2$;
Example 126: D-Phe-cyclo[Cys-Tyr-D-Pal-Lys-Val-Cys]-Thr-N $H_2$;
Example 127: Ac-D-Nal-cyclo[Cys-Tyr-D-Trp-Lys-Val-Cys]-Thr-N $H_2$;
Example 128: D-Phe-cyclo[Cys-Tyr-D-Trp-Lys-Val-Cys]-Nal-$NH_2$;
Example 129: D-Nal-cyclo[Cys-Tyr-D-Trp-Lys-Val-Cys]-Nal-$NH_2$;
Example 130: D-Nal-cyclo[Cys-Tyr-D-Trp-Lys-Val-Cys]-Thr-OH;

Example 131: D-Phe-cyclo[Cys-Nal-D-Trp-Lys-Val-Cys]-Thr-NH$_2$;
Example 132: D-Nal-cyclo[Cys-Tyr-D-Nal-Lys-Val-Cys]-Nal-NH$_2$;
Example 133: D-Nal-cyclo[Cys-Tyr-D-Trp-Lys-Val-D-Cys]-Nal-NH$_2$;
Example 134: D-Trp-cyclo[Cys-Tyr-D-Trp-Lys-Val-Cys]-Nal-NH$_2$;
Example 135: D-Nal-cyclo[Cys-Tyr-D-Trp-Lys-Val-Cys]-D-Nal-NH$_2$;
Example 136: Nal-cyclo[Cys-Tyr-D-Trp-Lys-Val-Cys]-D-Nal-NH$_2$;
Example 137: (AcO-CH$_2$)$_3$—C—NH—CO—(CH$_2$)$_2$-CO-D-Nal-cyclo(Cys-Tyr-D-Trp-Lys-Val-Cys]Thr—NH$_2$;
Example 138:[3-O-(2,5,6-triacetyl ascorbic)acetyl-D-Nal-cyclo[Cys-Tyr-D-Trp-Lys-Val-Cys]-Thr—NH$_2$;
Example 139: D-Nal-cyclo[Cys-Tyr-D-Trp-Lys-Val-Cys]-Trp-NH$_2$;
Example 140: Phe-cyclo[Cys-Tyr-D-Trp-Lys-Val-Cys]-Trp-NH$_2$;
Example 141: 3-O-(ascorbic)-butryrl-D-Nal-cyclo[Cys-Tyr-D-Trp-Lys-Val-Cys]-Thr-NH$_2$;
Example 142: 3-O-(ascorbic acid)Ac-D-Nal-cyclo[Cys-Tyr-D-Trp-Lys-Val-Cys]-Thr—NH$_2$;
Example 143: D-Bpa-cyclo[Cys-Tyr-D-Trp-Lys-Val-Cys]-Nal-NH$_2$;
Example 144: D-Nal-cyclo[Cys-Tyr-D-Trp-Lys-Val-Cys]-Bpa-NH$_2$;
Example 145: Tris- Suc-D-Nal-cyclo[Cys-Tyr-D-Trp-Lys-Val-Cys]-Thr-N H$_2$;
Example 146: D-Dpa-cyclo[Cys-Tyr-D-Trp-Lys-Val-Cys]-Nal-NH$_2$;
Example 147: D-Nal-cyclo[Cys-Tyr-D-Trp-Lys-Val-Cys]-Dpa-NH$_2$;
Example 148: Ac-D-Nal-cyclo[Cys-Tyr-D-Trp-Lys-Val-Cys]-Thr-NH$_2$; and
Example 149: cyclo-[Cys-Tyr-D-Trp-Lys-Val-Cys]-Thr—NH$_2$.

Somatostatin Receptor Binding Assays

The human SSTR-1, SSTR-2, SSTR-3, SSTR-4, and SSTR-5 cDNA clones have been described (SSTR-1 and SSTR-2 in Yamada, Y., et al., Proc. Natl. Acad. Sci. USA, 89:251–255 (1992); SSTR-3 in Yamada, et al., Mol. Endocrinol. 6:2136–2142 (1993); and SSTR-4 and SSTR-5 in Yamada, et al., Biochem. Biophys. Res. Commun. 195:844–852 (1993)) and are also available from American Type Culture Collection (ATCC, Rockville, Md.) (ATCC Nos. 79044 (SSTR-1), 79046 (SSTR-2), and 79048 (SSTR-3)). Based on the restriction endonuclease maps, the entire coding region of each SSTR cDNA may be excised by suitable restriction endonuclease digestion (Maniatis, T., et al., *Molecular Cloning—A Laboratory Manual*, CSHL, 1982). Restriction endonucleases are available from New England Biolabs (Beverly, Mass.). This cDNA fragment was inserted into the mammalian expression vector, pCMV (Russell, D., et al., J. Biol. Chem., 264:8222–8229 (1989)), using standard molecular biology techniques (see e.g., Maniatis, T., et al., Molecular Cloning,—A Laboratory Manual, Cold Spring Harbor Laboratory, 1982) to produce the expression plasmid, pCMV-human SSTR-1 through pCMV-human SSTR-5. Other mammalian expression vectors include pcDNA1/Amp (Invitrogen, Sandlesy, Calif.). The expression plasmids were introduced into the suitable bacterial host, *E. Coli* HB101 (Stratagene, La Jolla, Calif.) and plasmid DNAs, for transfection, were prepared on Cesium Chloride gradients.

CHO-K1 (ovary, Chinese hamster) cells were obtained from ATCC (ATCC No. CCL 61). The cells were grown and maintained in Ham's F12 media (Gibco BRL, Grand Island, N.Y.) supplemented with 10% fetal bovine serum under standard tissue culture conditions. For transfection, the cells were seeded at a density 1×10$^6$/60-cm plate (Baxter Scientific Products, McGraw Park, Ill.). DNA mediated transfection was carried out using the calcium phosphate co-precipitation method (Ausubel, F. M., et al., Current Protocols in Molecular Biology, John Wiley & Sons, 1987). The plasmid pRSV-neo (ATCC; ATCC No. 37198) was included as a selectable marker at 1/10 the concentration of the expression plasmid. CHO-K1 clonal cell lines that have stably inherited the transfected DNA were selected for growth in Ham's F12 media containing 10% fetal bovine serum and 0.5 mg/ml of G418 (Sigma). The cells were ring-cloned and expanded in the same media for analysis.

Expression of the human SSTR-1 through SSTR-5 receptors in the CHO-K1 cells were detected by Northern blot analysis of total RNA prepared from the cells (Sambrook, J. E., et al., Molecular Cloning—A Laboratory Manual, Ed. 2., Cold Spring Harbor Laboratory, Cold Spring Harbor, N.Y., 1989) and by receptor binding using [$^{125}$I-Tyr$^{11}$] somatostatin-14 as a ligand. Transfected cell lines expressing the human SSTR receptors were clonally expanded in culture and used in the following SSTR binding protocol.

Crude membranes were prepared by homogenization of the transfected cells in 20 ml of ice-cold 50 mM Tris-HCl with a POLYTRON homogenizer (setting 6, 15 sec). Buffer was added to obtain a final volume of 40 ml, and the homogenate was centrifuged in a Sorval SS-34 rotor at 39,000 g for about 10 min at about 0–4° C. The resulting supernatant was decanted and discarded. The pellet was rehomogenized in ice-cold buffer, diluted, and centrifuged as before. The final pellet was resuspended in 10 mM Tris HCl and held on ice for the receptor binding assay.

Aliquots of the membrane preparation were incubated for about 30 min at about 30° C. with 0.05 nM [$^{125}$I-Tyr$^{11}$] somatostatin-14 (2000 Ci/mmol; Amersham Corp., Arlington Heights, Ill.) in 50 mM HEPES (pH 7.4) containing a test somatostatin agonist of various concentrations (e.g., 10$^{-11}$ to 10$^{-6}$), 10 mg/ml bovine serum albumin (fraction V) (Sigma Chemical Co., St. Louis, Mo.), MgCl$_2$ (5 mM), Trasylol (200 KIU ml), bacitracin (0.02 mg/ml), and phenylmethylsulphonyl fluoride (0.02 mg/ml). The final assay volume was 0.3 ml. The incubations were terminated by rapid filtration through GF/C filters (pre-soaked in 0.3% polyethyleneimine for 30 min) using a Brandel filtration manifold. Each tube and filter were then washed three times with 5 ml aliquots of ice-cold buffer. Specific binding was defined as the total [$^{125}$I-Tyr$^{11}$]SRIF-14 bound minus that bound in the presence of 1000 nM unlabelled SRIF-14. The Ki values for the tested somatostatin agonists were calculated by using the following formula: Ki=IC$_{50}$/[1+(LC/LEC)] where IC$_{50}$ is the concentration of test somatostatin agonist required to inhibit 50 percent of the specific binding of the radioligand [$^{125}$-Tyr$^{11}$] somatostatin-14, LC is the concentration of the radioligand (0.05 nM), and LEC is the equilibrium dissociation constant of the radioligand (0.16 nM). The Ki values (nM) for the tested somatostatin agonists are shown in Table 1.

TABLE 1

|  | hSSTR-1 | hSSTR-2 | hSSTR-3 | hSSTR-4 | hSSTR-5 |
|---|---|---|---|---|---|
| Somatostatin-14 | 2.26 | 0.23 | 1.2 | 1.8 | 1.41 |
| Somatostatin-28 | 2.38 | 0.30 | 1.3 | 7.93 | 0.4 |
| Example 1 | 2414 | 0.75 | 97.9 | 1826 | 5.21 |
| Example 12 | 875 | 0.57 | 26.8 | 5029 | 6.78 |
| Example 107 | 1227 | 15.06 | 545 | 3551 | 0.42 |
| Example 108 | 27.9 | 19.3 | 35.6 | 58.6 | 0.85 |
| Example 109 | 86.9 | 6.19 | 9.7 | 3.4 | 0.34 |
| Example 110 | 15.1 | 4.78 | 25.5 | 55.3 | 0.30 |
| Example 114 | 97.6 | 11.96 | 5.6 | 127 | 1.22 |
| Example 118 | 47.7 | 3.23 | 10.9 | 753 | 1.01 |
| Example 120 | 9120 | 0.35 | 215 | 7537 | 11.1 |
| Example 121 | 6016 | 0.19 | 26.8 | 3897 | 9.81 |

A somatostatin agonist that is used in a method of this invention can be assessed for its ability to inhibit H. pylori proliferation by testing it in the following assay.

Bacteria: The following three standard H. pylori strains were utilized: ATCC43504, NCTC11638, NCTC11916. The latter two strains were generous gifts from Dr. Takashi Shimoyama & Dr. Norihiro Fukuda (Hyogo College of Medicine, Nishinomiya, Japan) but are also commercially available from such companies as the American Type Culture Collection (Manassas, Va.).

Culture: H. pylori was cultured in Brucella broth (Becton Dickinson, Co. Ltd., Tokyo, Japan) containing 7% fetal bovine serum (FBS: GIBCO-BRL, Grand Island, N.Y.) at about 37° C. in a microaerobic atmosphere (5% $O_2$, 15% $CO_2$, 80% $N_2$) with a relative humidity of greater than 98% in the incubator (TE-HA $O_2$-$CO_2$ incubator $CPO_2$-171; Hirasawa Works, Co. Ltd., Tokyo, Japan).

Compounds and Treatment: The following compounds were tested: synthetic somatostatin (Peptide Institute, Osaka, Japan), Example 76 (high affinity for type 2), Example 114 (high affinity for types 3 & 5), Example 107 (high affinity for type 5 with some affinity for types 1 & 3) and Example 109 (high affinity for types 2, 3 & 4). Compounds are dissolved in absolute methanol (Katayama Chemical Industries, Co. Ltd., Osaka, Japan) immediately before the experiments. Various concentrations of compounds in absolute methanol or methanol alone (vehicle) at 50 µL is added into 5 mL of Brucella broth immediately before H. pylori inoculation into the broth, resulting in a final methanol concentration of approximately 1% (by volume). From the fundamental study (see hereinbelow), methanol at a level used in this assay does not modify H. pylori proliferation and makes compounds sufficiently sterile, that is free from any other microorganisms.

Bacteria counting: H. pylori is cultured in Brucella broth to confluence for 5 days (109 CFU/mL), and 50 µL of Brucella broth containing 5×$10^3$ CFU of H. pylori is inoculated to a fresh 5 mL Brucella broth. This procedure keeps the H. pylori applied to the broth constant at approximately 103 CFU/mL in the broth at the starting point. Bacteria number (CFU/mL) 48 h after compound application into the Brucella broth is calculated by counting the colonies on trypticase soy agar containing 5% sheep blood (Becton Dickinson) 5 days after inoculation of H. pylori containing broth at several different dilution rates onto the plate under the same culture conditions mentioned above.

Effect of compounds on H. pylori proliferation and pH of the broth: Various concentrations of somatostatin dissolved in 50 µL absolute methanol or vehicle alone were added into the Brucella broth inoculated ATCC43504 at $10^3$ CFU/mL. Final compound levels investigated ranged from $10^{-14}$ mol/L through $10^{-6}$ mol/L. Bacteria number is examined 48 h after the incubation. Effect of Examples 76, 107, 109 and 114 at $10^{-11}$ mol/L on ATCC43504 proliferation and an effect of somatostatin at $10^{-11}$ mol/L on two other strains of H. pylori proliferation were also tested. The pH of the supernatant of the 48 hour-long-cultured broth is measured by a digital pH meter (Beckman Instruments, Co. Ltd., Fullerton, Calif.).

Effect of immunoneutralization of SSTR-1 or SSTR-2 on somatostatin action on H. pylori proliferation: The influence of purified IgG against SSTR-1 peptide [41-52] (SSTR-1-Ab: 1.0 g/mL), IgG against SSTR-2 peptide [31-41] (SSTR-2-Ab: 1.0 µg/mL) produced and characterized in our laboratory (Endocrine Regul. 29:189,1995 & 30:67,1996) or IgG from non-immune rabbit serum (Control-IgG:1.0 µg/mL) on somatostatin ($10^{-11}$ mol/L)-induced antiproliferative effect on H. pylori is tested.

Stability of compounds in the broth: The synthetic somatostatin in the Brucella broth at a final peptide concentration of 10 ng/mL was incubated for 0, 1, 4, 24 and 48 hours under the same culture conditions. Somatostatin is extracted from bacteria-free Brucella broth by the methanol method and measured by radioimmunoassay as reported previously (Kaneko et al., Dig. Dis. Sci., 1992, 37, 409–416). Values are expressed as percent recovery rates of the peptide.

Microscopic findings of H. pylori after somatostatin application: Light microscopic feature of ATCC 43504 in the Brucella broth (Gram stain) is observed 48 hours after incubation with either vehicle or somatostatin ($10^{-11}$ mol/L).

Effect of somatostatin on protein levels in the broth: Protein levels in the supernatant of the cultured broth incubated for 48 hours with ATCC43504 at an initial concentration of $10^3$ CFU/mL and somatostatin ($10^{-11}$–$10^{-6}$ mol/L) are measured with the Micro BCA Protein Assay Reagent Kit (Pierce, Co. Ltd., Rockford, Ill.) by a spectrophotometer (U3200; Hitachi, Co. Ltd., Tokyo, Japan).

Effect of somatostatin on gamma glutamyl transpeptidase (γ-GTP) levels in the broth: Levels of γ-GTP in the supernatant of the following Brucella broth incubated for 48 hours are measured by γ-GT IFCC Kit (Boehringer-Mannheim, Co. Ltd., Tokyo, Japan); Group A: Brucella broth alone, Group B: Brucella broth plus ATCC43504, Group C: Brucella broth with ATCC43504 plus somatostatin ($10^{-11}$ mol/L) and Group D: extensive sonication (10 kHz, 3 min) done in group B by Heat System Ultrasonics; Microson (Nisonix, Co. Ltd., Farmingdale, N.Y.). γ-GTP level in the supernatant of the broth is a marker of bacteria destruction, because genomic DNA and amino acid sequence of γ-GTP has been detected. In addition, lactate dehydrogenase (LDH), a popular indicator of cell destruction, is not suited for the present assay as LDH in the Brucella broth itself showed relatively high concentration (approximately 20 IU/L) which makes it difficult to detect the changes in LDH levels in other groups.

Statistics: Results are expressed as the mean SEM. The differences between the control and experimental subgroups are determined by the analysis of variance (Bonferroni). Comparisons between two groups in pH are performed by Mann-Whitney U test. A probability level of P<0.05 is considered significant.

Results

Effect of chemicals on H. pylori proliferation: Somatostatin inhibited proliferation of ATCC43504 in a dose-dependent manner, and somatostatin achieved a minimally statistically significant effect at $10^{-11}$ mol/L, where bacteria number decreased by 49% (P<0.01) (Table 2).

Examples 76 and 109 dramatically suppressed proliferation by 89% and 79%, respectively (P<0.01). Example 107

(P<0.05) also showed an antiproliferative effect. Example 114 had no effect at the tested concentration.

Somatostatin at $10^{-11}$ mol/L also significantly inhibited NCTC11638 and NCTC11916 by 90% and 79%, respectively ($\times 10^6$ CFU/mL; NCTC11638, vehicle: 15.4±0.9, somatostatin: 1.6±0.2; NCTC11916, vehicle: 12.0±1.0, somatostatin: 2.6±0.2; P<0.01, n=6).

TABLE 2

Effect of somatostatin (SS) on ATCC43504 proliferation

| SS Concentration (log M) | ATCC43504 ($\times 10^7$ CFU/mL) | No. of Samples |
|---|---|---|
| Vehicle | 5.9 ± 0.6 | 14 |
| −14 | 5.2 ± 0.6 | 10 |
| −13 | 5.3 ± 0.7 | 10 |
| −12 | 4.2 ± 0.4 | 12 |
| −11 | 3.0 ± 0.4* | 10 |
| −10 | 2.1 ± 0.2* | 10 |
| −8 | 1.9 ± 0.3* | 10 |
| −6 | 1.9 ± 0.3* | 12 |

(Data are expressed as the mean±SEM of samples. *P<0.01 compared with vehicle treatment)

TABLE 3

Effect of somatostatin analogs on ATCC43504 proliferation

| Chemicals ($10^{-11}$ mol/L) | ATCC43504 ($\times 10^5$ CFU/mL) |
|---|---|
| Vehicle | 12.8 ± 1.8 |
| Example 114 | 9.8 ± 2.0 |
| Example 107 | 6.5 ± 0.7* |
| Example 76 | 2.7 ± 1.3** |
| Example 109 | 1.4 ± 0.5** |

(Data are expressed as the mean ± SEM of 5 samples. *P < 0.05, **P < 0.01 compared with vehicle treatment.)

Effect of immunoneutralization of SSTR-1 or SSTR-2 on somatostatin action on *H. pylori* proliferation: Neither SSTR-1-Ab nor SSTR-2-Ab itself modified *H. pylori* proliferation. In Control-IgG treated group, somatostatin inhibited *H. pylori* proliferation by 88%. This antiproliferative effect of somatostatin was significantly blocked by SSTR-2-Ab co-incubation by 52% (P<0.05). SSTR-1-Ab had no effect.

TABLE 4

Effect of immunoneutralization on somatostatin-induced antiproliferative effect

| Antibody | Control-IgG | | SSTR-1-Ab | | SSTR-2-Ab | |
|---|---|---|---|---|---|---|
| Compound | Vehicle | SS | Vehicle | SS | Vehicle | SS |
| ATCC43504 ($\times 10^6$ CFU/mL) | 25.0 ± 2.8 | 3.0 ± 1.1* | 23.7 ± 8.7 | 1.8 ± 0.5* | 23.8 ± 6.9 | 14.5 ± 2.8# |
| No. of samples | 6 | 6 | 4 | 6 | 6 | 6 |

(Data are expressed as the mean ± SEM of samples. *-P < 0.01 vs respective vehicle, #-P < 0.05 vs Control-IgG + SS)

Fundamental assay (this assay establishes that a decrease in *H. pylori* number (CFU) was induced by the antiproliferative effect of somatostatin and not by the somatostatin-induced changes in broth pH, nutrient conditions, forms of *H. pylori* to coccoid or by destruction of *H. pylori*): The pH in the Brucella broth incubated for 48 hours with ATCC43504 was 6.9±0.1. Somatostatin at $10^{-11}$ mol/L did not modify the pH of the broth (7.0±0.1; n=6). Somatostatin levels in the Brucella broth gradually decreased, but were almost stable, up to 48 hours after administration (mean %; somatostatin: 0 hr, 102.8%; 4 hrs, 94.8%; 24 hrs, 81.7%; 48 hrs, 80.1%; n=4, P<0.01). Morphologic conversion of *H. pylori* from bacillary to non culturable coccoid form was not observed 48 hours after incubation with somatostatin at $10^{-11}$ mol/L. Somatostatin at levels at or above $10^{-11}$ mol/L did not affect protein levels in the 48 hour long broth incubation with ATCC43504 (mg/mL; vehicle:17.2±1.5, $10^{-11}$ mol/L: 16.8±0.2, $10^{-10}$ mol/L: 16.0±1.0, $10^{-8}$ mol/L: 19.1±0.6, $10^{-6}$ mol/L: 15.4±1.0; n=4). Gamma-GTP was only detected in the supernatant of group D (10.5±0.5 IU/L, n=4) in which ATCC43504 cultured for about 48 hours was sonicated. In contrast, γ-GTP levels were zero in group A, B and C.

A compound as described hereinabove which is to be used in a method the present invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound as described hereinabove which is to be used in a method of the present invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

The dosage of a compound as described hereinabove to be used in a method of the present invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 mg/kg to 100 mg/kg of body weight daily are administered to humans and other animals, e.g., mammals.

A preferred dosage range is 0.01 mg/kg to 5.0 mg/kg of body weight daily which can be administered as a single dose or divided into multiple doses.

What is claimed is:

1. A method of inhibiting the proliferation of *Helicobacter pylori* in a patient in need thereof, which comprises administering to said patient an effective amount of somatostatin or a somatostatin agonist or a pharmaceutically acceptable salt thereof.

2. A method according to claim 1 wherein somatostatin or a pharmaceutically acceptable salt thereof is administered to said patient.

3. A method according to claim 1 wherein a somatostatin agonist or a pharmaceutically acceptable salt thereof is administered to said patient.

4. A method according to claim 3 wherein said somatostatin agonist is a somatostatin sub-type receptor 2 selective agonist or a pharmaceutically acceptable salt thereof.

5. A method according to claim 4 wherein said somatostatin sub-type receptor 2 selective agonist is cyclo(N-Me-Ala-Tyr-D-Trp-Lys-Val-Phe) or H-D-β-Nal-Cys-Tyr-D-Trp-Lys-Thr-Cys-Thr-NH$_2$ or a pharmaceutically acceptable salt thereof.

6. A method according to claim 3 wherein said somatostatin agonist is H-Cys-Phe-Phe-D-Trp-Lys-Thr-Phe-Cys-NH$_2$ or H-Cys-Phe-Tyr-D-Trp-Lys-Thr-Phe-Cys-NH$_2$ or a pharmaceutically acceptable salt thereof.

7. A method according to claim 3 wherein said somatostatin agonist is:

H-D-Phe-Cys-Phe-D-Trp-Lys-Thr-Cys-β-Nal-NH$_2$,

H-D-Phe-Cys-Tyr-D-Trp-Lys-Thr-Cys-β-Nal-NH$_2$,
H-D-P-Nal-Cys-Phe-D-Trp-Lys-Thr-Cys-Thr-NH$_2$,
H-D-Phe-Cys-Tyr-D-Trp-Lys-Thr-Pen-Thr-NH$_2$,
H-D-Phe-Cys-Phe-D-Trp-Lys-Thr-Pen-Thr-NH$_2$,
H-D-Phe-Cys-Tyr-D-Trp-Lys-Thr-Pen-Thr-OH,
H-D-Phe-Cys-Phe-D-Trp-Lys-Thr-Pen-Thr-OH,
H-Gly-Pen-Phe-D-Trp-Lys-Thr-Cys-Thr-OH,
H-Phe-Pen-Tyr-D-Trp-Lys-Thr-Cys-Thr-OH,
H-Phe-Pen-Phe-D-Trp-Lys-Thr-Pen-Thr-OH,
H-D-Phe-Cys-Phe-D-Trp-Lys-Thr-Cys-Thr-ol,
H-D-Phe-Cys-Phe-D-Trp-Lys-Thr-Cys-Thr—NH$_2$,
H-D-Trp-Cys-Tyr-D-Trp-Lys-Val-Cys-Thr-N H$_2$,
H-D-Trp-Cys-Phe-D-Trp-Lys-Thr-Cys-Thr-N H$_2$,
H-D-Phe-Cys-Tyr-D-Trp-Lys-Val-Cys-Thr—NH$_2$,
H-D-Phe-Cys-Tyr-D-Trp-Lys-Val-Cys-Trp-N H$_2$,
H-D-Phe-Cys-Tyr-D-Trp-Lys-Val-Cys-Thr—NH$_2$,
Ac-D-Phe-Lys*-Tyr-D-Trp-Lys-Val-Asp*-Thr—NH$_2$ (an amide bridge formed between Lys* and Asp*),
Ac-hArg(Et)$_2$-Gly-Cys-Phe-D-Trp-Lys-Thr-Cys-Thr-N H$_2$,
Ac-D-hArg(Et)$_2$-Gly-Cys-Phe-D-Trp-Lys-Thr-Cys-Thr—NH$_2$,
Ac-D-hArg(Bu)-Gly-Cys-Phe-D-Trp-Lys-Thr-Cys-Thr—NH$_2$,
Ac-D-hArg(Et)$_2$-Cys-Phe-D-Trp-Lys-Thr-Cys-Thr—NH$_2$,
Ac-L-hArg(Et)$_2$-Cys-Phe-D-Trp-Lys-Thr-Cys-Thr—NH$_2$,
Ac-D-hArg(CH$_2$CF$_3$)$_2$-Cys-Phe-D-Trp-Lys-Thr-Cys-Thr-N H$_2$,
Ac-D-hArg(CH$_2$CF$_3$)$_2$-Gly-Cys-Phe-D-Trp-Lys-Thr-Cys-Thr-N H$_2$,
Ac-D-hArg(CH$_2$CF$_3$)$_2$-Gly-Cys-Phe-D-Trp-Lys-Thr-Cys-Phe-NH$_2$,
Ac-D-hArg(CH$_2$CF$_3$)$_2$-Gly-Cys-Phe-D-Trp-Lys-Thr-Cys-Thr-NHEt,
Ac-L-hArg(CH$_2$—CF$_3$)$_2$-Gly-Cys-Phe-D-Trp-Lys-Thr-Cys-Thr-NH$_2$,
Ac-D-hArg(CH$_2$CF$_3$)$_2$-Gly-Cys-Phe-D-Trp-Lys(Me)-Thr-Cys-Thr—NH$_2$,
Ac-D-hArg(CH$_2$CF$_3$)$_2$-Gly-Cys-Phe-D-Trp-Lys(Me)-Thr-Cys-Thr—NHEt,
Ac-hArg(CH$_3$, hexyl)-Gly-Cys-Phe-D-Trp-Lys-Thr-Cys-Thr—NH$_2$,
H-hArg(hexyl$_2$)-Gly-Cys-Phe-D-Trp-Lys-Thr-Cys-Thr-NH$_2$,
Ac-D-hArg(Et)$_2$-Gly-Cys-Phe-D-Trp-Lys-Thr-Cys-Thr-NHEt,
Ac-D-hArg(Et)$_2$-Gly-Cys-Phe-D-Trp-Lys-Thr-Cys-Phe-NH$_2$,
Propionyl-D-hArg(Et)$_2$-Gly-Cys-Phe-D-Trp-Lys(iPr)-Thr-Cys-Thr-NH$_2$,
Ac-D-β-Nal-Gly-Cys-Phe-D-Trp-Lys-Thr-Cys-Gly-hArg (Et)$_2$-N H$_2$,
Ac-D-Lys(iPr)-Gly-Cys-Phe-D-Trp-Lys-Thr-Cys-Thr—NH$_2$,
Ac-D-hArg(CH$_2$CF$_3$)$_2$-D-hArg(CH$_2$CF$_3$)$_2$-Gly-Cys-Phe-D-Trp-Lys-Thr-Cys-Thr-N H$_2$,
Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$, Ac-D-hArg(Et)$_2$-D-hArg(Et)$_2$-Gly-Cys-Phe-D-Trp-Lys-Thr-Cys-Thr-NH$_2$,
Ac-Cys-Lys-Asn-4-Cl-Phe-Phe-D-Trp-Lys-Thr-Phe-Thr-Ser-D-Cys-NH$_2$,
H-Bmp-Tyr-D-Trp-Lys-Val-Cys-Thr-hr-NH$_2$,
H-Bmp-Tyr-D-Trp-Lys-Val-Cys-Phe-NH$_2$,
H-Bmp-Tyr-D-Trp-Lys-Val-Cys-p-Cl-Phe-NH$_2$,
H-Bmp-Tyr-D-Trp-Lys-Val-Cys-β-Nal-NH$_2$,
H-D-β-Nal-Cys-Tyr-D-Trp-Lys-Val-Cys-Thr—NH$_2$,
H-D-Phe-Cys-Tyr-D-Trp-Lys-Abu-Cys-Thr—NH$_2$,
H-D-Phe-Cys-Tyr-D-Trp-Lys-Abu-Cys-β-N al-N H$_2$,
H-pentafluoro-D-Phe-Cys-Tyr-D-Trp-Lys-Val-Cys-Thr-N H$_2$,
Ac-D-β-Nal-Cys-pentafluoro-Phe-D-Trp-Lys-Val-Cys-Thr-NH$_2$,
H-D-β-Nal-Cys-Tyr-D-Trp-Lys-Val-Cys-β-Nal-NH$_2$,
H-D-Phe-Cys-Tyr-D-Trp-Lys-Val-Cys-β-Nal-NH$_2$,
H-D-β-Nal-Cys-Tyr-D-Trp-Lys-Abu-Cys-Thr—NH$_2$,
H-D-p-Cl-Phe-Cys-Tyr-D-Trp- Lys-Abu-Cys-Thr-NH$_2$,
Ac-D-p-Cl-Phe-Cys-Tyr-D-Trp-Lys-Abu-Cys-Thr—NH$_2$,
H-D-Phe-Cys-β-Nal-D-Trp-Lys-Val-Cys-Thr-NH$_2$,
H-D-Phe-Cys-Tyr-D-Trp-Lys-Cys-Thr—NH$_2$,
cyclo(Pro-Phe-D-Trp-N-Me-Lys-Thr-Phe),
cyclo(Pro-Phe-D-Trp-N-Me-Lys-Thr-Phe),
cyclo(Pro-Phe-D-Trp-Lys-Thr-N-Me-Phe),
cyclo(N-Me-Ala-Tyr-D-Trp-Lys-Thr-Phe),
cyclo(Pro-Tyr-D-Trp-Lys-Thr-Phe),
cyclo(Pro-Phe-D-Trp-Lys-Thr-Phe),
cyclo(Pro-Phe-L-Trp-Lys-Thr-Phe),
cyclo (Pro-Phe-D-Trp(F)-Lys-Thr-Phe),
cyclo(Pro-Phe-Trp(F)-Lys-Thr-Phe),
cyclo(Pro-Phe-D-Trp-Lys-Ser-Phe),
cyclo(Pro-Phe-D-Trp-Lys-Thr-p-Cl-Phe),
cyclo(D-Ala-N-Me-D-Phe-D-Thr-D-Lys-Trp-D-Phe),
cyclo(D-Ala-N-Me-D-Phe-D-Val-Lys-D-Trp-D-P he),
cyclo(D-Ala-N-Me-D-Phe-D-Thr-Lys-D-Trp-D-Phe),
cyclo(D-Ala-N-Me-D-Phe-D-Thr-Lys-D-Trp-D-Phe),
cyclo(D-Abu-N-Me-D-Phe-D-Val-Lys-D-Trp-D-Tyr),
cyclo(D-Ala-N-Me-D-Phe-D-Thr-Lys-D-Trp-D-Phe),
cyclo(Pro-Tyr-D-Trp-t-4-AchxAla-Thr-Phe),
cyclo(Pro-Phe-D-Trp-t-4-AchxAla-Thr-Phe),
cyclo(N-Me-Ala-Tyr-D-Trp-t-4-AchxAla-Thr-Phe),
cyclo(Pro-Tyr-D-Trp-4-Amphe-Thr-Phe),
cyclo(Pro-Phe-D-Trp-4-Amphe-Thr-Phe),
cyclo(N-Me-Ala-Tyr-D-Trp-4-Amphe-Thr-Phe),
cyclo(Asn-Phe-Phe-D-Trp-Lys-Thr-Phe-Gaba),
cyclo(Asn-Phe-Phe-D-Trp-Lys-Thr-Phe-Gaba-Gaba),
cyclo(Asn-Phe-D-Trp-Lys-Thr-Phe),
cyclo(Asn-Phe-Phe-D-Trp-Lys-Thr-Phe-NH(CH$_2$)$_4$CO),
cyclo(Asn-Phe-Phe-D-Trp-Lys-Thr-Phe-β-Ala),
cyclo(Asn-Phe-Phe-D-Trp-Lys-Thr-Phe-D-Glu)-OH,
cyclo(Phe-Phe-D-Trp-Lys-Thr-Phe),
cyclo(Phe-Phe-D-Trp-Lys-Thr-Phe-Gly),
cyclo(Phe-Phe-D-Trp-Lys-Thr-Phe-Gaba),
cyclo(Asn-Phe-Phe-D-Trp-Lys-Thr-Phe-Gly),
cyclo(Asn-Phe-Phe-D-Trp(F)-Lys-Thr-Phe-Gaba),
cyclo(Asn-Phe-Phe-D-Trp(NO$_2$)-Lys-Thr-Phe-Gaba),
cyclo(Asn-Phe-Phe-Trp(Br)-Lys-Thr-Phe-Gaba),
cyclo(Asn-Phe-Phe-D-Trp-Lys-Thr-Phe(.)-Gaba),
cyclo(Asn-Phe-Phe-D-Trp-Lys-Thr-Tyr(But)-Gaba),
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Tpo-Cys)-OH,
cyclo(Bmp-Lys-Asn-Phe-Phe-D-Trp-Lys-Thr-Phe-Thr-MeLeu-Cys)-OH,
cyclo( Phe-Phe-D-Trp-Lys-Thr-Phe-Phe-Gaba),
cyclo(Phe-Phe-D-Trp-Lys-Thr-Phe-D-Phe-Gaba),
cyclo(Phe-Phe-D-Trp(5F)-Lys-Thr-Phe-Phe-Gaba),
cyclo(Asn-Phe-Phe-D-Trp-Lys(Ac)-Thr-Phe-NH-(CH$_2$)$_3$—CO),
cyclo(Lys-Phe-Phe-D-Trp-Lys-Thr-Phe-Gaba),
cyclo(Lys-Phe-Phe-D-Trp-Lys-Thr-Phe-Gaba),
cyclo(Orn-Phe-Phe-D-Trp-Lys-Thr-Phe-Gaba),
H-Cys-Phe-Phe-D-Trp-Lys-Ser-Phe-Cys-NH$_2$,
H-Cys-Phe-Tyr(l)-D-Trp-Lys-Thr-Phe-Cys-NH$_2$,
D-Cpa-cyclo[Cys-Tyr-D-Trp-Lys-Val-Cys]-Thr-NH$_2$,
D-Phe-cyclo[Cys-Tyr-D-Trp-Lys-Val-Cys]-Thr-NH$_2$,
D-Phe-cyclo[Cys-p-NH$_2$-Phe-D-Trp-Lys-Val-Cys]-Thr-NH$_2$,
N-Me-D-Phe-cyclo[Cys-Tyr-D-Trp-Lys-Val-cys]-Thr-NH$_2$,
D-Phe-cyclo[Cys-Tyr-D-Pal-Lys-Val-Cys]-Thr-NH$_2$,
Ac-D-Nal-cyclo[Cys-Tyr-D-Trp-Lys-Val-Cys]-Thr-NH$_2$,
D-Phe-cyclo[Cys-Tyr-D-Trp-Lys-Val-Cys]-Nal-NH$_2$,
D-Nal-cyclo[Cys-Tyr-D-Trp-Lys-Val-Cys]-Nal-NH$_2$,
D-Nal-cyclo[Cys-Tyr-D-Trp-Lys-Val-Cys]-Thr-OH,
D-Phe-cyclo[Cys-Nal-D-Trp-Lys-Val-Cys]-Thr-NH$_2$,
D-Nal-cyclo[Cys-Tyr-D-Nal-Lys-Val-Cys]-Nal-NH$_2$,
D-Nal-cyclo[Cys-Tyr-D-Trp-Lys-Val-D-Cys]-Nal-NH$_2$,
D-Trp-cyclo[Cys-Tyr-D-Trp-Lys-Val-Cys]-Nal-NH$_2$,
D-Nal-cyclo[Cys-Tyr-D-Trp-Lys-Val-Cys]-D-Nal-NH$_2$,
Nal-cyclo[Cys-Tyr-D-Trp-Lys-Val-Cys]-D-Nal-NH$_2$,
(AcO-CH$_2$)$_3$-C-N H-CO-(CH$_2$)$_2$-CO-D-Nal-cyclo(Cys-Tyr-D-Trp-Lys-Val-Cys]Thr-NH$_2$,
[3-O-(2,5,6-triacetyl ascorbic)acetyl-D-Nal-cyclo[Cys-Tyr-D-Trp-Lys-Val-Cys]-Thr-NH$_2$,
D-Nal-cyclo[Cys-Tyr-D-Trp-Lys-Val-Cys]-Trp-NH$_2$,
Phe-cyclo[Cys-Tyr-D-Trp-Lys-Val-Cys]-Trp-NH$_2$,
3-O-(ascorbic)-butryrl-D-Nal-cyclo[Cys-Tyr-D-Trp-Lys-Val-Cys]-Thr-NH$_2$,
3-O-(ascorbic acid)Ac-D-Nal-cyclo[Cys-Tyr-D-Trp-Lys-Val-Cys]-Thr-NH$_2$,
D-Bpa-cyclo[Cys-Tyr-D-Trp-Lys-Val-Cys]-Nal-NH$_2$,
D-Nal-cyclo[Cys-Tyr-D-Trp-Lys-Val-Cys]-Bpa-NH$_2$,
Tris- Suc-D-Nal-cyclo[Cys-Tyr-D-Trp-Lys-Val-Cys]-Thr-NH$_2$,
D-Dpa-cyclo[Cys-Tyr-D-Trp-Lys-Val-Cys]-Nal-NH$_2$,
D-Nal-cyclo[Cys-Tyr-D-Trp-Lys-Val-Cys]-Dpa-NH$_2$,
Ac-D-Nal-cyclo[Cys-Tyr-D-Trp-Lys-Val-Cys]-Thr-NH$_2$ or
cyclo-[Cys-Tyr-D-Trp-Lys-V-al-Cys]-Thr-NH$_2$, or a pharmaceutically acceptable salt thereof.

8. A method according to claim 3 wherein said somatostatin agonist is of the formula (I),

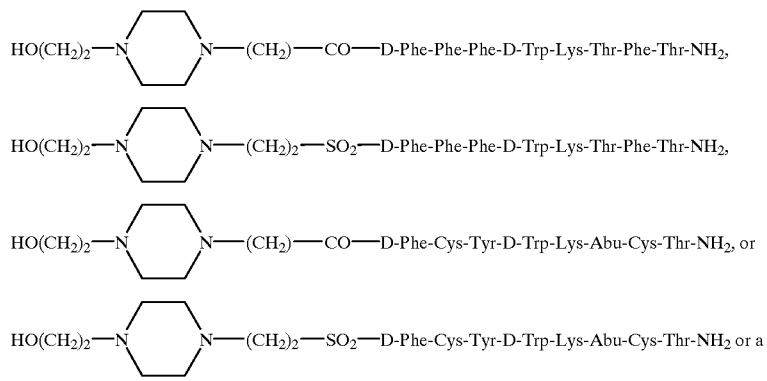

or a pharmaceutically acceptable salt thereof.

11. A method according to claim 3 wherein said somatostatin agonist is a compound of the formula (II),

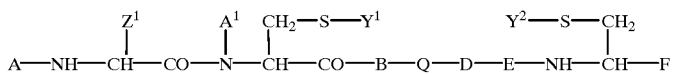

(II)

or a pharmaceutically acceptable salt thereof,
wherein

A is hydrogen, $(C_1-C_3)$alkyl, $(C_1-C_4)$alkanoyl;

$Z^1$ is $-(CH_2)_n$Ar wherein Ar is an aromatic side chain moiety of an aromatic amino acid or a lipophilic side chain portion of a lipophilic amino acid, wherein the aromatic side chain moiety is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy; n is 1, 2 or 3;

$A^1$ is hydrogen or $(C_1-C_3)$alkyl;

$Y^1$ and $Y^2$ are each independently hydrogen;

or $Y^1$ and $Y^2$ are taken together to form a bond between the sulfur atoms to which they are attached;

B is an aromatic amino acid wherein the aromatic side chain moiety is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy;

Q is L- or D-Trp which is optionally substituted in the benzene ring by F, Cl, Br, $NO_2$, $NH_2$, OH, $(C_1-C_3)$alkyl or $(C_1-C_3)$alkoxy;

H-D-Phe-p-chloro-Phe-Tyr-D-Trp-Lys-Thr-Phe-Thr-NH$_2$,
H-D-Phe-p-NO$_2$-Phe-Tyr-D-Trp-Lys-Val-Phe-Thr-NH$_2$,
H-D-p-Nal-p-chloro-Phe-Tyr-D-Trp-Lys-Val-Phe-Thr-NH$_2$,
H-D-Phe-Phe-Tyr- D-Trp-Lys-Val- Phe-Thr-NH$_2$,
H-D-Phe-p-chloro-Phe-Tyr-D-Trp-Lys-Val-Phe-Thr-NH$_2$, or
H-D-Phe-Ala-Tyr-D-Trp-Lys-Val-Ala-D-P-Nal-NH$_2$, or a pharmaceutically acceptable salt thereof.

10. A method according to claim 3 wherein said somatostatin agonist is (I)

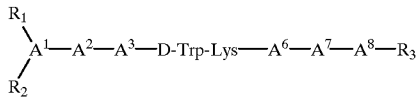

or a pharmaceutically acceptable salt thereof wherein $A^1$ is a D- or L- isomer of Ala, Leu, Ile, Val, Nle, Thr, Ser, β-Nal, β-Pal, Trp, Phe, 2,4-dichloro-Phe, pentafluoro-Phe, p-X-Phe, or o-X-Phe, wherein X is CH$_3$, Cl, Br, F, OH, OCH$_3$ or NO$_2$;

$A^2$ is Ala, Leu, Ile, Val, Nle, Phe, P-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^3$ is pyridyl-Ala, Trp, Phe, P-Nal, 2,4-dichloro-Phe, pentafluoro-Phe, o-X-Phe, or p-X-Phe, wherein X is CH$_3$, Cl, Br, F, OH, OCH$_3$ or NO$_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each $R_1$ and $R_2$, independently, is H, lower acyl or lower alkyl; and $R_3$ is OH or NH$_2$.

9. A method according to claim 8 where the somatostatin agonist is

D is Lys or Orn wherein the a-amino group is optionally substituted by methyl and the δ-NH$_2$ is optionally substituted by (C$_1$-C$_3$)alkyl;

E is Ser, Thr or an amino acid having a side chain moiety which is (C$_1$-C$_5$)alkyl, (C$_5$-C$_7$)cycloalkyl-(C$_1$-C$_2$) alkyl or -(CH$_2$)$_m$-Aryl wherein m is 1, 2 or 3 and the Aryl is phenyl, naphthyl, indolyl or a heterocyclyl group which is a 5 or 6 membered aromatic ring where one or more carbons are replaced with N, O or S, where the Aryl is optionally substituted by one to five substituents each independently selected from the group consisting of halogen, NO$_2$, NH$_2$, OH, (C$_1$-C$_3$)alkyl and (C$_1$-C$_3$)alkoxy;

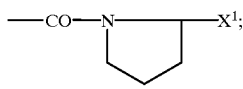

F is COOR$^1$, CH$_2$OR$^2$, CO—NR$^3$R$^4$ or wherein R$^1$ is hydrogen or (C$_1$-C$_3$)alkyl; R$^2$ is hydrogen or the radical of a physiologically acceptable, physiologically hydrolyzable ester; R$^3$ is hydrogen, (C$_1$-C$_3$) alkyl, phenyl or phenyl-(C$_1$-C$_3$)alkyl, provided that when R$^4$ is —CH(R$^5$)—X$^1$ then R$^3$ can only be hydrogen or (C$_1$-C$_3$)alkyl; R$^4$ is hydrogen, (C$_1$-C$_3$)alkyl or —CH(R$^5$)—X$^1$; R$^5$ is the side chain of a natural amino acid, HO—(CH$_2$)$_2$- or HO—(CH$_2$)$_3$—; X$^1$ is COOR$^1$, CH$_2$OR$^2$ or CO-NR$^6$R$^7$; R$^6$ is hydrogen or (C$_1$-C$_3$) alkyl;

R$^7$ is hydrogen, (C$_1$-C$_3$)alkyl, phenyl or phenyl-(C$_1$-C$_3$) alkyl.

12. A method according to claim 3 wherein said somatostatin agonist is a compound of the formula (III), (III)

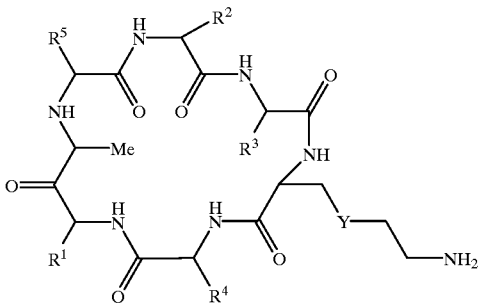

or a pharmaceutically acceptable salt thereof,
wherein

Y is (CH$_2$)$_m$ wherein m is 0, 1 or 2 or sulfur such that the sulfur may be in any position along the chain;

R$^1$ and R$^2$ are independently (C$_1$-C$_5$)alkyl, benzyl, substituted benzyl where the substituent may be one or two of (C$_1$-C$_5$)alkyl, halogen, hydroxy, amino, nitro or (C$_1$-C$_5$) alkoxy; and (C$_1$-C$_5$)alkyl substituted with a 5- or 6-membered heterocyclic ring having 1 or 2 heteroatoms selected from the group consisting of O, N and S;

R$^3$ is 3-indolylmethyl or substituted 3-indolylmethyl wherein the substituent may be (C$_1$-C$_5$)alkyl, (C$_1$-C$_5$) alkoxy or halogen;

R$^4$ is (C$_1$-C$_5$)alkyl, hydroxy-(C$_1$-C$_5$)alkyl, benzyl, carboxy-(C$_1$-C$_5$)alkyl, amino-(C$_1$-C$_5$)alkyl or substituted benzyl wherein the substituent may be (C$_1$-C$_5$) alkyl, (C$_1$-C$_5$)alkoxy, hydroxy, halogen, amino or nitro; and R$^5$ is hydrogen, (C$_1$-C$_5$)alkyl, benzyl, or substituted benzyl wherein the substituent is (C$_1$-C$_5$)alkyl, (C$_1$-C$_5$) alkoxy, hydroxy, halogen, amino or nitro.

13. A method of treating a medical disorder mediated by the proliferation of *Helicobacter pylori* in a patient in need thereof, which comprises administering an effective amount of somatostatin or a somatostatin agonist or a pharmaceutically acceptable salt thereof to said patient.

14. A method according to claim 13 wherein the medical disorder is peptic ulcer disease, mucosa associated lymphoid tissue lymphoma, gastritis with severe abnormality, post early gastric cancer resection, gastric cancer and gastric lymphoma.

15. A method according to claim 13 wherein somatostatin or a pharmaceutically acceptable salt thereof is administered.

16. A method according to claim 15 wherein the medical disorder is peptic ulcer disease, mucosa-associated lymphoid tissue lymphoma, gastritis with severe abnormality, post early gastric cancer resection, gastric cancer and gastric lymphoma.

17. A method according to claim 13 wherein a somatostatin agonist or a pharmaceutically acceptable salt thereof is administered.

18. A method according to claim 17 wherein the medical disorder is peptic ulcer disease, mucosa-associated lymphoid tissue lymphoma, gastritis with severe abnormality, post early gastric cancer resection, gastric cancer and gastric lymphoma.

19. A method according to claim 17 wherein said somatostatin agonist is a somatostatin sub-type 2 receptor selective agonist or a pharmaceutically acceptable salt thereof.

20. A method according to claim 19 wherein the medical disorder is peptic ulcer disease, mucosa-associated lymphoid tissue lymphoma, gastritis with severe abnormality, post early gastric cancer resection, gastric cancer and gastric lymphoma.

21. A method according to claim 19 wherein said somatostatin sub-type receptor 2 selective agonist is cyclo(N-Me-Ala-Tyr-D-Trp-Lys-Val-Phe) or H-D-P-Nal-Cys-Tyr-D-Trp-Lys-Thr-Cys-Thr-NH$_2$ or a pharmaceutically acceptable salt thereof.

22. A method according to claim 21 wherein the medical disorder is peptic ulcer disease, mucosa-associated lymphoid tissue lymphoma, gastritis with severe abnormality, post early gastric cancer resection, gastric cancer and gastric lymphoma.

23. A method according to claim 17 wherein said somatostatin agonist is H-Cys-Phe-Phe-D-Trp-Lys-Thr-Phe-Cys-NH$_2$ or H-Cys-Phe-Tyr-D-Trp-Lys-Thr-Phe-Cys-NH$_2$ or a pharmaceutically acceptable salt thereof.

24. A method according to claim 23 wherein the medical disorder is peptic ulcer disease, mucosa-associated lymphoid tissue lymphoma, gastritis with severe abnormality, post early gastric cancer resection, gastric cancer and gastric lymphoma.

25. A method according to claim 17 wherein said somatostatin agonist is:

H-D-Phe-Cys-Phe-D-Trp-Lys-Thr-Cys-β-Nal-NH$_2$,
H-D-Phe-Cys-Tyr-D-Trp-Lys-Thr-Cys-β-Nal-NH$_2$,
H-D-P-Nal-Cys-Phe-D-Trp-Lys-Thr-Cys-Thr-NH$_2$,
H-D-Phe-Cys-Tyr-D-Trp-Lys-Thr-Pen-Thr-NH$_2$,
H-D-Phe-Cys-Phe-D-Trp-Lys-Thr-Pen-Thr-NH$_2$,

H-D-Phe-Cys-Tyr-D-Trp-Lys-Thr-Pen-Thr-OH,
H-D-Phe-Cys-Phe-D-Trp-Lys-Thr-Pen-Thr-OH,
H-Gly-Pen-Phe-D-Trp-Lys-Th r-Cys-Thr-O H,
H-Phe-Pen-Tyr-D-Trp-Lys-Thr-Cys-Thr-OH,
H-Phe-Pen-Phe-D-Trp-Lys-Thr-Pen-Thr-OH,
H-D-Phe-Cys-Phe-D-Trp-Lys-Thr-Cys-Thr-ol,
H-D-Phe-Cys-Phe-D-Trp-Lys-Thr-Cys-Thr-NH$_2$,
H-D-Trp-Cys-Tyr-D-Trp-Lys-Val-Cys-Thr-NH$_{21}$
H-D-Trp-Cys-Phe-D-Trp-Lys-Thr-Cys-Thr-NH$_2$,
H-D-Phe-Cys-Tyr-D-Trp-Lys-Val-Cys-Thr-NH$_2$,
H-D-Phe-Cys-Tyr-D-Trp-Lys-Val-Cys-Trp-NH$_2$,
H-D-Phe-Cys-Tyr-D-Trp-Lys-Val-Cys-Thr-NH$_2$,
Ac-D-Phe-Lys*-Tyr-D-Trp-Lys-Val-Asp*-Thr-NH$_2$ (an amide bridge formed between Lys* and Asp*),
Ac-hArg(Et)$_2$-Gly-Cys-Phe-D-Trp-Lys-Thr-Cys-Thr-NH$_2$,
Ac-D-hArg(Et)$_2$-Gly-Cys-Phe-D-Trp-Lys-Thr-Cys-Thr-NH$_2$,
Ac-D-hArg(Bu)-Gly-Cys-Phe-D-Trp-Lys-Thr-Cys-Thr-NH$_2$,
Ac-D-hArg(Et)$_2$-Cys-Phe-D-Trp-Lys-Thr-Cys-Thr-NH$_2$,
Ac-L-hArg(Et)$_2$-Cys-Phe-D-Trp-Lys-Thr-Cys-Thr-NH$_2$,
Ac-D-hArg(CH$_2$CF$_3$)$_2$-CYS-Phe-D-Trp-Lys-Thr-Cys-Thr-NH$_2$,
Ac-D-hArg(CH$_2$CF$_3$)$_2$-Gly-Cys-Phe-D-Trp-Lys-Thr-Cys-Thr-NH$_2$,
Ac-D-hArg(CH$_2$CF$_3$)$_2$-Gly-Cys-Phe-D-Trp-Lys-Thr-Cys-Phe-NH$_2$,
Ac-D-hArg(CH$_2$CF$_3$)2-Gly-Cys-Phe-D-Trp-Lys-Thr-Cys-Thr-NHEt,
Ac-L-hArg(CH$_2$-CF$_3$)$_2$-Gly-Cys-Phe-D-Trp-Lys-Thr-Cys-Thr-NH$_2$,
Ac-D-hArg(CH$_2$CF$_3$)$_2$-Gly-Cys-Phe-D-Trp-Lys(Me)-Thr-Cys-Thr-NH$_2$,
Ac-D-hArg(CH$_2$CF$_3$)$_2$-Gly-Cys-Phe-D-Trp-Lys(Me)-Thr-Cys-Thr-NHEt,
Ac-hArg(CH$_3$, hexyl)-Gly-Cys-Phe-D-Trp-Lys-Thr-Cys-Thr-NH$_2$,
H-hArg(hexyl$_2$)-Gly-Cys-Phe-D-Trp-Lys-Thr-Cys-Thr-NH$_2$,
Ac-D-hArg(Et)$_2$-Gly-Cys-Phe-D-Trp-Lys-Thr-Cys-Thr-NHEt,
Ac-D-hArg(Et)$_2$-Gly-Cys-Phe-D-Trp-Lys-Thr-Cys-Phe-NH$_2$,
Propionyl-D-hArg(Et)$_2$-Gly-Cys-Phe-D-Trp-Lys(iPr)-Thr-Cys-Thr-NH$_2$,
Ac-D-β-Nal-Gly-Cys-Phe-D-Trp-Lys-Thr-Cys-Gly-hArg(Et)$_2$-NH$_2$,
Ac-D-Lys(iPr)-Gly- Cys-Phe-D-Trp-Lys-Thr-Cys-Thr-NH$_2$,
Ac-D-hArg(CH$_2$CF$_3$)$_2$-D-hArg(CH$_2$CF$_3$)$_2$-Gly-Cys-Phe-D-Trp-Lys-Thr-Cys-Thr-NH$_2$,
Ac-D-hArg (CH$_2$CF$_3$)$_2$-D-hArg(CH$_2$CF$_3$)$_2$-Gly-Cys-Phe-D-Trp-Lys-Thr-Cys-Phe-NH$_2$,
Ac-D-hArg(Et)$_2$-D-hArg(Et)$_2$-Gly-Cys-Phe-D-Trp-Lys-Thr-Cys-Thr-NH$_2$,
Ac-Cys-Lys-Asn-4-Cl-Phe-Phe-D-Trp-Lys-Thr-Phe-Thr-Ser-D-Cys-NH$_2$,
H-Bmp-Tyr-D-Trp-Lys-Val-Cys-Thr-NH$_2$,
H-Bmp-Tyr-D-Trp-Lys-Val-Cys-Phe-NH$_2$,
H-Bmp-Tyr-D-Trp-Lys-Val-Cys-p-CI-Phe-NH$_2$,
H-Bmp-Tyr-D-Trp-Lys-Val-Cys-p-Nal-N H$_2$,
H-D-β-Nal-Cys-Tyr-D-Trp-Lys-Val-Cys-Thr-NH$_2$,
H-D-Phe-Cys-Tyr-D-Trp-Lys-Abu-Cys-Thr-NH$_2$,
H-D-Phe-Cys-Tyr-D-Trp-Lys-Abu-Cys-β-Nal-NH$_2$,
H-pentafluoro-D-Phe-Cys-Tyr-D-Trp-Lys-Val-Cys-Thr-NH$_2$,
Ac-D-β-Nal-Cys-pentafluoro-Phe-D-Trp-Lys-Val-Cys-Thr-NH$_2$,
H-D-β-Nal-Cys-Tyr-D-Trp-Lys-Val-Cys-β-Nal-NH$_2$,
H-D-Phe-Cys-Tyr-D-Trp-Lys-Val-Cys-β-Nal-NH$_2$,
H-D-β-Nal-Cys-Tyr-D-Trp-Lys-Abu-Cys-Thr-NH$_2$,
H-D-p-Cl-Phe-Cys-Tyr-D-Trp-Lys-Abu-Cys-Thr-NH$_2$,
Ac-D-p-Cl-Phe-Cys-Tyr-D-Trp-Lys-Abu-Cys-Thr-NH$_2$,
H-D-Phe-Cys-β-Nal-D-Trp-Lys-Val-Cys-Thr-NH$_2$,
H-D-Phe-Cys-Tyr-D-Trp-Lys-Cys-Thr-NH$_2$,
cyclo(Pro-Phe-D-Trp-N-Me-Lys-Thr-Phe),
cyclo(Pro-Phe-D-Trp-N-Me-Lys-Thr-Phe),
cyclo(Pro-Phe-D-Trp-Lys-Thr-N-Me-Phe),
cyclo(N-Me-Ala-Tyr-D-Trp-Lys-Thr-Phe),
cyclo(Pro-Tyr-D-Trp-Lys-Thr-Phe),
cyclo(Pro-Phe-D-Trp-Lys-Thr-Phe),
cyclo(Pro-Phe-L-Trp-Lys-Thr-Phe),
cyclo(Pro-Phe-D-Trp(F)-Lys-Thr-Phe),
cyclo(Pro-Phe-Trp(F)-Lys-Thr-Phe),
cyclo(Pro-Phe-D-Trp-Lys-Ser-Phe),
cyclo(Pro-Phe-D-Trp-Lys-Thr-p-C-Phe),
cyclo(D-Ala-N-Me-D-Phe-D-Thr-D-Lys-Trp-D-Phe),
cyclo(D-Ala-N-Me-D-Phe-D-Val-Lys-D-Trp-D-Phe),
cyclo(D-Ala-N-Me-D-Phe-D-Thr-Lys-D-Trp-D-Phe),
cyclo(D-Abu-N-Me-D-Phe-D-Val-Lys-D-Trp-D-Tyr),
cyclo(Pro-Tyr-D-Trp-t-4-AchxAla-Thr-Phe ),
cyclo(Pro-Phe-D-Trp-t-4-AchxAla-Thr-Phe),
cyclo(N-Me-Ala-Tyr-D-Trp-t-4-AchxAla-Thr-Phe),
cyclo(Pro-Tyr-D-Trp-4-Amphe-Thr-Phe),
cyclo(Pro-Phe-D-Trp-4-Amphe-Thr-Phe),
cyclo(N-Me-Ala-Tyr-D-Trp-4-Amphe-Thr-Phe),
cyclo(Asn-Phe-Phe-D-Trp-Lys-Thr-Phe-Gaba),
cyclo(Asn-Phe-Phe-D-Trp-Lys-Thr-Phe-Gaba—Gaba),
cyclo(Asn-Phe-D-Trp-Lys-Thr-Phe),
cyclo(Asn-Phe-Phe-D-Trp-Lys-Thr-Phe-NH(CH$_2$)$_4$CO),
cyclo(Asn-Phe-Phe-D-Trp-Lys-Thr-Phe-β-Ala),
cyclo(Asn-Phe-Phe-D-Trp-Lys-Thr-Phe-D-Glu)-OH,
cyclo(Phe-Phe-D-Trp-Lys-Thr-Phe),
cyclo(Phe-Phe-D-Trp-Lys-Thr-Phe-Gly),
cyclo(Phe-Phe-D-Trp-Lys-Thr-Phe-Gaba),
cyclo(Asn-Phe-Phe-D-Trp-Lys-Thr-Phe-Gly),
cyclo(Asn-Phe-Phe-D-Trp(F)-Lys-Thr-Phe-Gaba),
cyclo(Asn-Phe-Phe-D-Trp(NO$_2$)-Lys-Thr-Phe-Gaba),
cyclo(Asn-Phe-Phe-Trp(Br)-Lys-Thr-Phe-Gaba),
cyclo(Asn-Phe-Phe-D-Trp-Lys-Thr-Phe(l)-Gaba),
cyclo(Asn-Phe-Phe-D-Trp-Lys-Thr-Tyr(But)-Gaba),
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Pro-Cys)-OH,
cyclo(Bmp-Lys-Asn-Phe-Phe-D-Trp-Lys-Thr-Phe-Thr-Tpo-Cys)-OH, cyclo(Bmp-Lys-Asn-Phe-Phe-D-Trp-Lys-Thr-Phe-Thr-MeLeu-Cys)-OH,
cyclo(Phe-Phe-D-Trp-Lys-Thr-Phe-Phe-Gaba),
cyclo(Phe-Phe-D-Trp-Lys-Thr-Phe-D-Phe-Gaba),
cyclo(Phe-Phe-D-Trp(5F)-Lys-Thr-Phe-Phe-Gaba),
cyclo(Asn-Phe-Phe-D-Trp-Lys(Ac)-Thr-Phe-NH-(CH$_2$)$_3$—CO),
cyclo(Lys-Phe-Phe-D-Trp-Lys-Thr-Phe-Gaba),
cyclo(Lys-Phe-Phe-D-Trp-Lys-Thr-Phe-Gaba),
cyclo(Orn-Phe-Phe-D-Trp-Lys-Thr-Phe-Gaba),
H-Cys-Phe-Phe-D-Trp-Lys-Ser-Phe-Cys-NH$_2$,
H-Cys-Phe-Tyr(l)-D-Trp-Lys-Thr-Phe-Cys-NH$_2$,
D-Cpa-cyclo[Cys-Tyr-D-Trp-Lys-Val-Cys]-Thr-NH$_2$,
D-Phe-cyclo[Cys-Tyr-D-Trp-Lys-Val-Cys]-Thr-NH$_2$,
D-Phe-cyclo[Cys-p-NH$_2$-Phe-D-Trp-Lys-Val-Cys]-Thr-NH$_2$,
N-Me-D-Phe-cyclo[Cys-Tyr-D-Trp-Lys-Val-Cys]-Thr-NH$_2$,
D-Phe-cyclo[Cys-Tyr-D-Pal-Lys-Val-Cys]-Thr-NH$_2$,
Ac-D-Nal-cyclo[Cys-Tyr-D-Trp-Lys-Val-Cys]-Thr-NH$_2$,
D-Phe-cyclo[Cys-Tyr-D-Trp-Lys-Val-Cys]-Nal-NH$_2$,
D-Nal-cyclo[Cys-Tyr-D-Trp-Lys-Val-Cys]-Nal-NH$_2$,
D-Nal-cyclo[Cys-Tyr-D-Trp-Lys-Val-Cys]-Thr-OH,
D-Phe-cyclo[Cys-Nal-D-Trp-Lys-Val-Cys]-Thr-NH$_2$,
D-Nal-cyclo[Cys-Tyr-D-Nal-Lys-Val-Cys]-Nal-NH$_2$,
D-Nal-cyclo[Cys-Tyr-D-Trp-Lys-Val-D-Cys]-Nal-NH$_2$,
D-Trp-cyclo[Cys-Tyr-D-Trp-Lys-Val-Cys]-Nal-NH$_2$,
D-Nal-cyclo[Cys-Tyr-D-Trp-Lys-Val-Cys]-D-Nal-NH$_2$,
Nal-cyclo[Cys-Tyr-D-Trp-Lys-Val-Cys]-D-Nal-NH$_2$,
(AcO-CH$_2$)$_3$-C—NH—CO-(CH$_2$)$_2$-CO-D-Nal-cyclo(Cys-Tyr-D-Trp-Lys-Val-Cys]Thr-NH$_2$,
[3-O-(2,5,6-triacetyl ascorbic)acetyl-D-Nal-cyclo[Cys-Tyr-D-Trp-Lys-Val-Cys]-Thr-NH$_2$,
D-Nal-cyclo[Cys-Tyr-D-Trp-Lys-Val-Cys]-Trp-NH$_2$,
Phe-cyclo[Cys-Tyr-D-Trp-Lys-Val-Cys]-Trp-NH$_2$,
3-O-(ascorbic)-butryrl-D-Nal-cyclo[Cys-Tyr-D-Trp-Lys-Val-Cys]-Thr-NH$_2$,
3-O-(ascorbic acid)Ac-D-Nal-cyclo[Cys-Tyr-D-Trp-Lys-Val-Cys]-Thr-NH$_2$,
D-Bpa-cyclo[Cys-Tyr-D-Trp-Lys-Val-Cys]-Nal-NH$_2$,
D-Nal-cyclo[Cys-Tyr-D-Trp-Lys-Val-Cys]-Bpa-NH$_2$,
Tris- Suc-D-Nal-cyclo[Cys-Tyr-D-Trp-Lys-Val-Cys]-Thr-NH$_2$,
D-Dpa-cyclo[Cys-Tyr-D-Trp-Lys-Val-Cys]-Nal-NH$_2$,
D-Nal-cyclo[Cys-Tyr-D-Trp-Lys-Val-Cys]-Dpa-NH$_2$,
Ac-D-Nal-cyclo[Cys-Tyr-D-Trp-Lys-Val-Cys]-Thr-NH$_2$ or
cyclo-[Cys-Tyr-D-Trp-Lys-Val-Cys]-Thr-NH$_2$, or a pharmaceutically acceptable salt thereof.

26. A method according to claim 25 wherein the medical disorder is peptic ulcer disease, mucosa-associated lymphoid tissue lymphoma, gastritis with severe abnormality, post early gastric cancer resection, gastric cancer and gastric lymphoma.

27. A method according to claim 17 wherein said somatostatin agonist is of the formula (I),

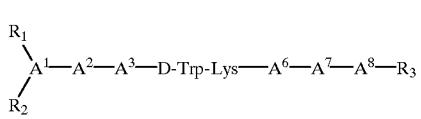

or a pharmaceutically acceptable salt thereof wherein

A$^1$ is a D-or L- isomer of Ala, Leu, Ile, Val, Nle, Thr, Ser, β-Nal, β-Pal, Trp, Phe, 2,4dichloro-Phe, pentafluoro-Phe, p-X-Phe, or o-X-Phe, wherein X is CH$_3$, Cl, Br, F, OH, OCH$_3$ or NO$_2$;

A$^2$ is Ala, Leu, Ile, Val, Nle, Phe, P-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^3$ is pyridyl-Ala, Trp, Phe, β-Nal, 2,4-dichloro-Phe, pentafluoro-Phe, o-X-Phe, or p-X-Phe, wherein X is CH$_3$, Cl, Br, F, OH, OCH$_3$ or NO$_2$;

A$^6$ is Val, Ala, Leu, Ile, Nle, Thr, Abu, or Ser;

A$^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is CH$_3$, Cl, Br, F, OH, OCH$_3$ or NO$_2$;

A$^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is CH$_3$, Cl, Br, F, OH, OCH$_3$ or NO$_2$;

each R$_1$ and R$_2$, independently, is H, lower acyl or lower alkyl; and R$_3$ is OH or NH$_2$.

28. A method according to claim 27 wherein the medical disorder is peptic ulcer disease, mucosa-associated lymphoid tissue lymphoma, gastritis with severe abnormality, post early gastric cancer resection, gastric cancer and gastric lymphoma.

29. A method according to claim 27 where the somatostatin agonist is

H-D-Phe-p-chloro-Phe-Tyr-D-Trp-Lys-Thr-Phe-Thr-NH$_2$,

H-D-Phe-p-NO$_2$-Phe-Tyr-D-Trp-Lys-Val-Phe-Thr-NH$_2$,

H-D-P-Nal-p-chloro-Phe-Tyr-D-Trp-Lys-Val-Phe-Thr-NH$_2$,

H-D-Phe-Phe-Tyr-D-Trp-Lys-Val-Phe-Thr-NH$_2$,

H-D-Phe-p-chloro-Phe-Tyr-D-Trp-Lys-Val-Phe-Thr-NH$_2$, or

H-D-Phe-Ala-Tyr-D-Trp-Lys-Val-Ala-D-P-Nal-NH$_2$, or a pharmaceutically acceptable salt thereof.

30. A method according to claim 29 wherein the medical disorder is peptic ulcer disease, mucosa-associated lymphoid tissue lymphoma, gastritis with severe abnormality, post early gastric cancer resection, gastric cancer and gastric lymphoma.

31. A method according to claim 17 wherein said somatostatin agonist is

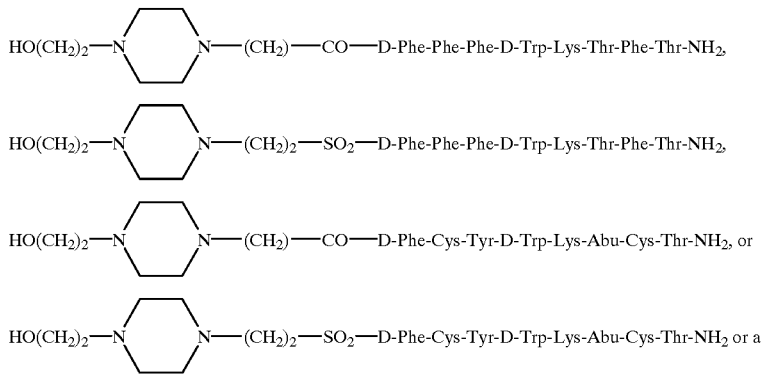

or a pharmaceutically acceptable salt thereof.

32. A method according to claim 31 wherein the medical disorder is peptic ulcer disease mucosa-associated lymphoid tissue lymphoma, gastritis with severe abnormality, post early gastric cancer resection, gastric cancer and gastric lymphoma.

33. A method according to claim 17 wherein said somatostatin agonist is a compound of the formula (II),

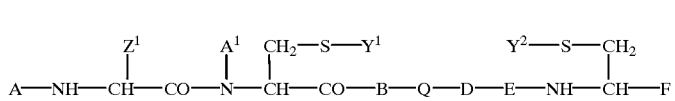

(II)

or a pharmaceutically acceptable salt thereof,
wherein

A is hydrogen, $(C_1-C_3)$alkyl, $(C_1-C_4)$alkanoyl;

$Z^1$ is —$(CH_2)_n$Ar wherein Ar is an aromatic side chain moiety of an aromatic amino acid or a lipophilic side chain portion of a lipophilic amino acid, wherein the aromatic side chain moiety is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy; n is 1, 2 or 3;

$A^1$ is hydrogen or $(C_1-C_3)$alkyl;

$Y^1$ and $Y^2$ are each independently hydrogen;

or $Y^1$ and $Y^2$ are taken together to form a bond between the sulfur atoms to which they are attached;

B is an aromatic amino acid wherein the aromatic side chain moiety is phenyl, naphthyl, indolyl or a heterocyclyl group which is a 5 or 6 membered aromatic ring where one or more carbons are replaced with N, O or S, and the aromatic side chain is optionally substituted by one to five substituents each independently selected from the group consisting of halogen, $NO_2$, $NH_2$, OH, $(C_1-C_3)$alkyl and $(C_1-C_3)$alkoxy;

Q is L- or D-Trp which is optionally substituted in the benzene ring by F, Cl, Br, $NO_2$, $NH_2$, OH, $(C_1-C_3)$alkyl or $(C_1-C_3)$alkoxy;

D is Lys or Orn wherein the a-amino group is optionally substituted by methyl and the δ-$NH_2$ is optionally substituted by $(C_1-C_3)$alkyl;

E is Ser, Thr or an amino acid having a side chain moiety which is $(C_1-C_5)$alkyl, $(C_5-C_7)$cycloalkyl-$(C_1-C_2)$alkyl or —$(CH_2)_m$-Aryl wherein m is 1, 2 or 3 and the Aryl is phenyl, naphthyl, indolyl or a heterocyclyl group which is a 5 or 6 membered aromatic ring where one or more carbons are replaced with N, O or S, where the Aryl is optionally substituted by one to five substituents each independently selected from the group consisting of halogen, $NO_2$, $NH_2$, OH, $(C_1-C_3)$alkyl and $(C_1-C_3)$alkoxy;

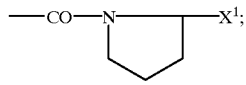

F is $COOR^1$, $CH_2OR^2$, $CO-NR^3R^4$ or ;

wherein $R^1$ is hydrogen or $(C_1-C_3)$alkyl; $R^2$ is hydrogen or the radical of a physiologically acceptable, physiologically hydrolyzable ester; $R^3$ is hydrogen, $(C_1-C_3)$alkyl, phenyl or phenyl-$(C_1-C_3)$alkyl, provided that when $R^4$ is —$CH(R^5)$—$X^1$ then $R^3$ can only be hydrogen or $(C_1-C_3)$alkyl; $R^4$ is hydrogen, $(C_1-C_3)$alkyl or —$CH(R^5)$—$X^1$; $R^5$ is the side chain of a natural amino acid, HO—$(CH_2)_2$— or HO—$(CH_2)_3$—; $X^1$ is $COOR^1$, $CH_2OR^2$ or $CO-NR^6R^7$; $R^6$ is hydrogen or $(C_1-C_3)$alkyl;

$R^7$ is hydrogen, $(C_1-C_3)$alkyl, phenyl or phenyl-$(C_1-C_3)$alkyl.

34. A method according to claim 33 wherein the medical disorder is peptic ulcer disease, mucosa-associated lymphoid tissue lymphoma, gastritis with severe abnormality, post early gastric cancer resection, gastric cancer and gastric lymphoma.

35. A method according to claim 17 wherein said somatostatin agonist is a compound of the formula (III), (III)

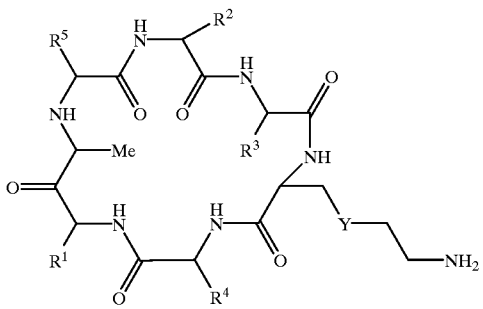

or a pharmaceutically acceptable salt thereof, wherein

Y is $(CH_2)_m$ wherein m is 0, 1 or 2 or sulfur such that the sulfur may be in any position along the chain;

$R^1$ and $R^2$ are independently $(C_1-C_5)$alkyl, benzyl, substituted benzyl where the substituent may be one or two of $(C_1-C_5)$alkyl, halogen, hydroxy, amino, nitro or $(C_1-C_5)$ alkoxy; and $(C_1-C_5)$alkyl substituted with a 5- or 6-membered heterocyclic ring having 1 or 2 heteroatoms selected from the group consisting of O, N and S;

$R^3$ is 3-indolylmethyl or substituted 3-indolylmethyl wherein the substituent may be $(C_1-C_5)$alkyl, $(C_1-C_5)$ alkoxy or halogen;

$R^4$ is $(C_1-C_5)$alkyl, hydroxy-$(C_1-C_6)$alkyl, benzyl, carboxy-$(C_1-C_5)$alkyl, amino-$(C_1-C_5)$alkyl or substituted benzyl wherein the substituent may be $(C_1-C_5)$ alkyl, $(C_1-C_5)$alkoxy, hydroxy, halogen, amino or nitro; and $R^5$ is hydrogen, $(C_1-C_5)$alkyl, benzyl, or substituted benzyl wherein the substituent is $(C_1-C_5)$alkyl, $(C_1-C_5)$ alkoxy, hydroxy, halogen, amino or nitro.

36. A method according to claim 35 wherein the medical disorder is peptic ulcer disease, mucosa-associated lymphoid tissue lymphoma, gastritis with severe abnormality, post early gastric cancer resection, gastric cancer and gastric lymphoma.

37. A pharmaceutical composition comprising an effective amount of somatostatin or a somatostatin agonist or a pharmaceutically acceptable salt thereof sufficient for inhibiting the proliferation of *Helicobacter pylori*, and a pharmaceutically acceptable carrier.

38. A pharmaceutical composition according to claim 37 wherein said somatostatin agonist is a somatostatin sub-type receptor 2 selective agonist or a pharmaceutically acceptable salt thereof.

39. A pharmaceutical composition according to claim 38 wherein said somatostatin sub-type receptor 2 selective agonist is cyclo(N-Me-Ala-Tyr-D-Trp-Lys-Val-Phe), H-D-P-Nal-Cys-Tyr-D-Trp-Lys-Thr-Cys-Thr-NH$_2$,

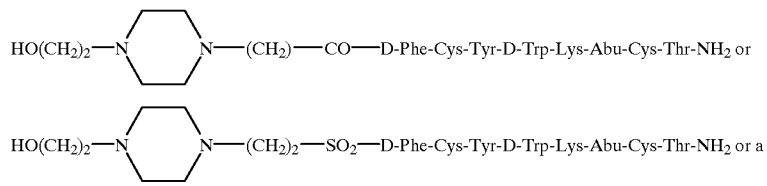

or a pharmaceutically acceptable salt thereof.

40. A pharmaceutical composition according to claim 37 wherein said somatostatin agonist is H-Cys-Phe-Phe-D-Trp-Lys-Thr-Phe-Cys-NH$_2$ or H-Cys-Phe-Tyr-D-Trp-Lys-Thr-Phe-Cys-NH$_2$, or a pharmaceutically acceptable salt thereof.

41. A pharmaceutical composition according to claim 37 comprising an effective amount of somatostatin or a pharmaceutically acceptable salt thereof sufficient to inhibit the proliferation of Helicobacter pylori, and a pharmaceutically acceptable carrier.

* * * * *